United States Patent
Kim

(10) Patent No.: US 8,828,035 B2
(45) Date of Patent: Sep. 9, 2014

(54) APPARATUS AND METHOD FOR PROSTATIC TISSUE REMOVAL

(75) Inventor: Daniel H. Kim, Houston, TX (US)

(73) Assignee: Urokinetics Inc., Houston, TX (US)

( * ) Notice: Subject to any disclaimer, the term of this patent is extended or adjusted under 35 U.S.C. 154(b) by 1321 days.

(21) Appl. No.: 11/969,587

(22) Filed: Jan. 4, 2008

(65) Prior Publication Data
US 2008/0188811 A1 Aug. 7, 2008

Related U.S. Application Data

(60) Provisional application No. 60/883,686, filed on Jan. 5, 2007.

(51) Int. Cl.
| | |
|---|---|
| A61B 17/32 | (2006.01) |
| A61B 17/3207 | (2006.01) |
| A61B 17/00 | (2006.01) |
| A61B 18/14 | (2006.01) |
| A61B 18/20 | (2006.01) |
| A61B 18/00 | (2006.01) |
| A61B 17/22 | (2006.01) |

(52) U.S. Cl.
CPC ............... *A61B 17/320725* (2013.01); *A61B 2017/320775* (2013.01); *A61B 2017/00867* (2013.01); *A61B 17/320758* (2013.01); *A61B 18/1485* (2013.01); *A61B 2017/00685* (2013.01); *A61B 18/20* (2013.01); *A61B 2018/00547* (2013.01); *A61B 2017/00274* (2013.01); *A61B 2017/22077* (2013.01)
USPC ............ 606/170; 606/167; 606/171; 606/180

(58) Field of Classification Search
USPC .......... 606/106, 108, 110, 114, 127, 128, 171, 606/180, 192, 32, 39, 45, 47, 48, 159, 167, 606/170; 604/261; 623/1.11
See application file for complete search history.

(56) References Cited

U.S. PATENT DOCUMENTS

| | | | | |
|---|---|---|---|---|
| 4,224,929 | A * | 9/1980 | Furihata | 600/116 |
| 4,946,449 | A * | 8/1990 | Davis, Jr. | 604/256 |
| 5,207,672 | A * | 5/1993 | Roth et al. | 606/10 |
| 5,588,965 | A * | 12/1996 | Burton et al. | 604/101.05 |
| 5,599,294 | A * | 2/1997 | Edwards et al. | 604/22 |
| 5,601,591 | A * | 2/1997 | Edwards et al. | 606/198 |
| 5,762,626 | A | 6/1998 | Lundquist et al. | |
| 5,957,922 | A | 9/1999 | Imran | |
| 6,102,886 | A | 8/2000 | Lundquist et al. | |
| 6,241,702 | B1 | 6/2001 | Lundquist et al. | |
| 6,445,957 | B1 * | 9/2002 | Bolmsjo | 607/101 |
| 6,491,672 | B2 * | 12/2002 | Slepian et al. | 604/267 |
| 6,514,247 | B1 | 2/2003 | McGaffigan et al. | |
| 6,682,555 | B2 * | 1/2004 | Cioanta et al. | 623/1.21 |
| 6,852,091 | B2 | 2/2005 | Edwards et al. | |
| 6,929,651 | B2 | 8/2005 | Huxel et al. | |
| 7,112,226 | B2 | 9/2006 | Gellman | |
| 7,399,290 | B2 * | 7/2008 | Maki et al. | 604/96.01 |
| 2006/0253007 | A1 | 11/2006 | Cheng et al. | |

OTHER PUBLICATIONS

PCT Search, International Application No. PCT/US 08/50259, dated May 20, 2008.

* cited by examiner

*Primary Examiner* — David Eastwood
(74) *Attorney, Agent, or Firm* — Patterson & Sheridan, L.L.P.

(57) ABSTRACT

Methods and apparatus for medical treating prostatic tissues are provided. In one embodiment, the method includes removing prostatic tissues adjacent the urethra and enlarging the lumen of the urethra, whereby the treatment conserves a natural wall of the urethra.

28 Claims, 29 Drawing Sheets

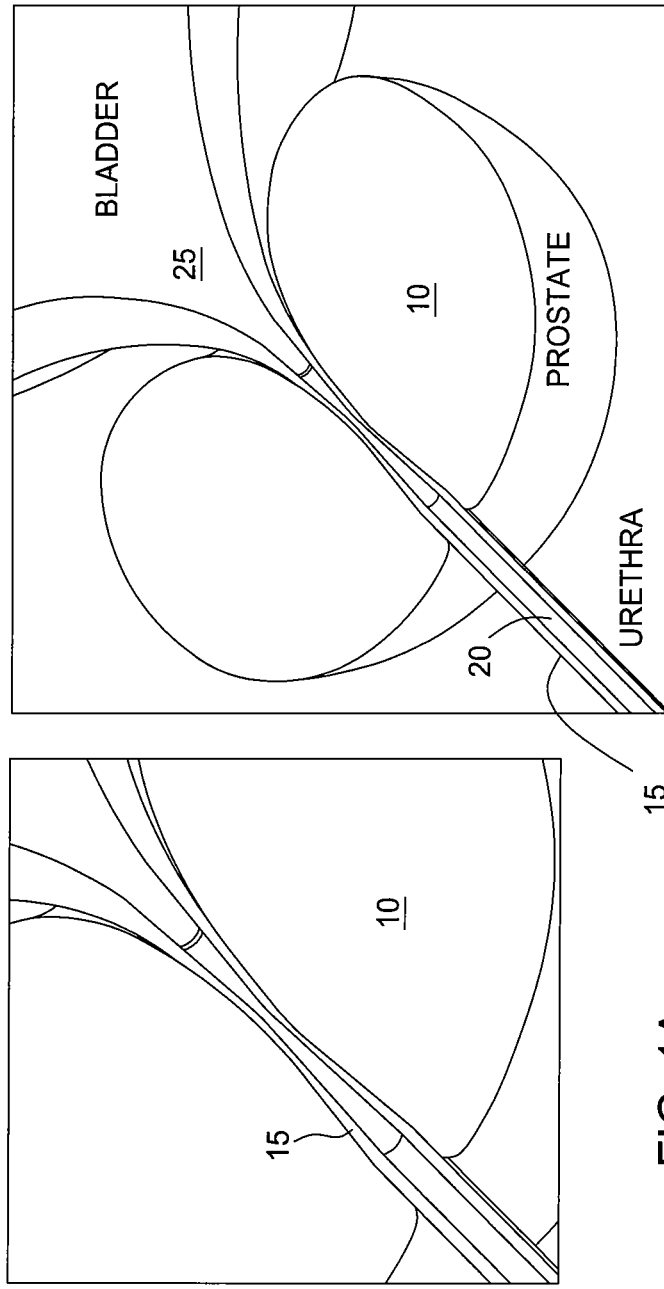

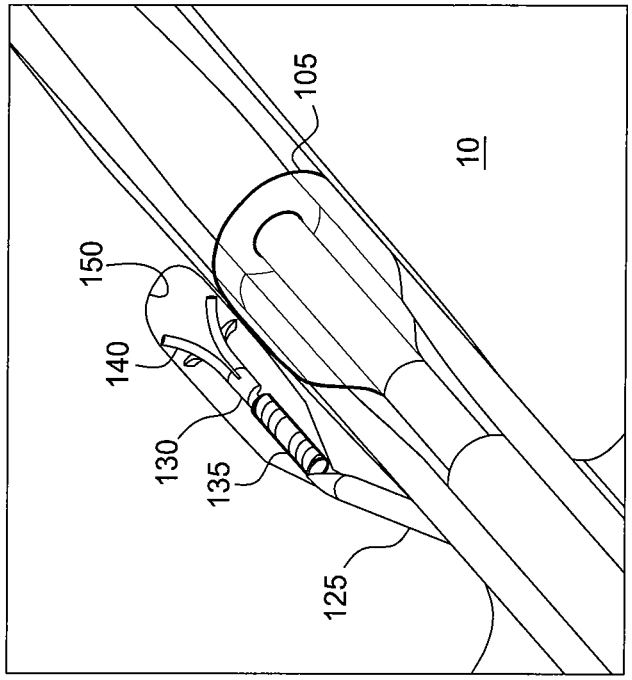
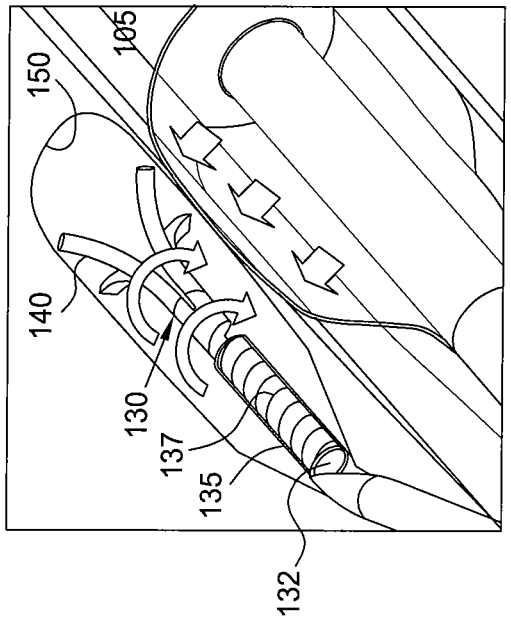
FIG. 6B
FIG. 6A

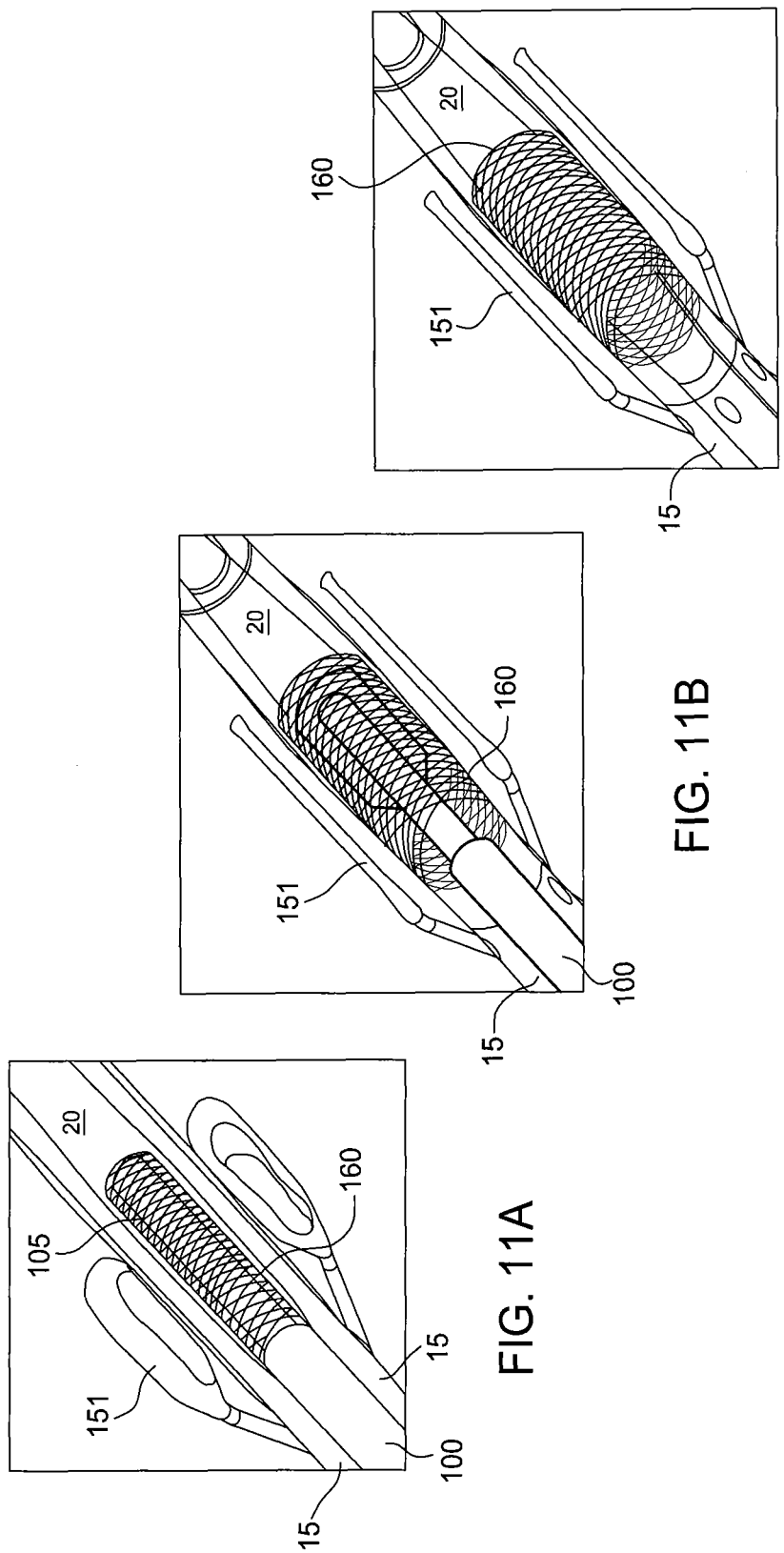

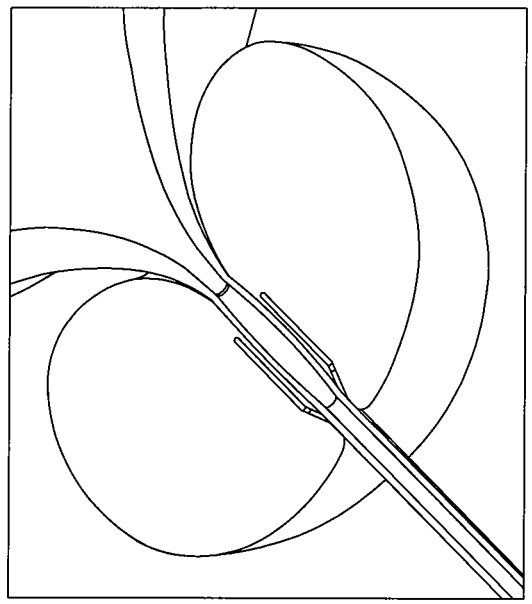
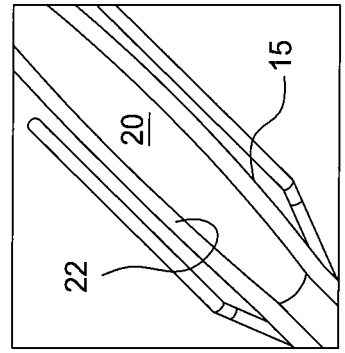
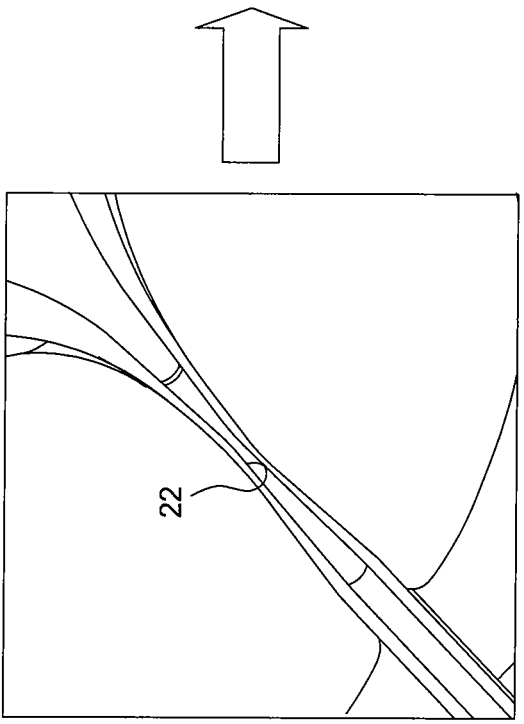
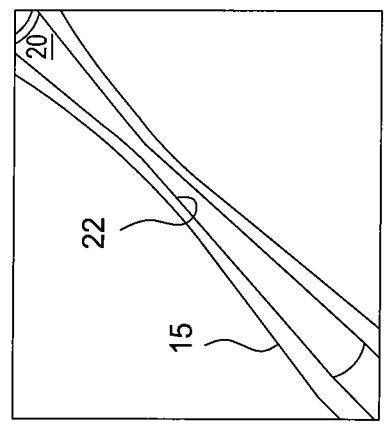
FIG. 13A
FIG. 13B

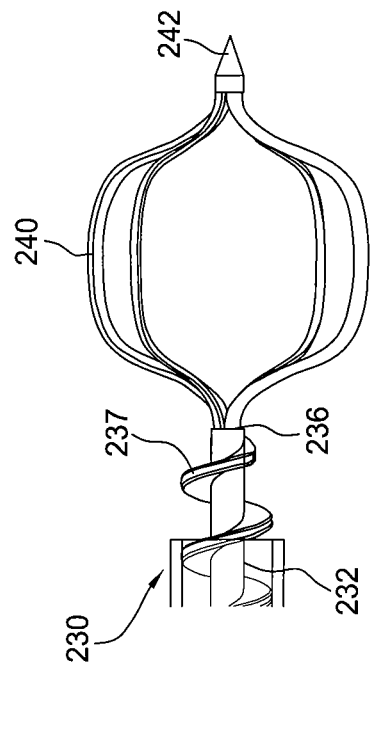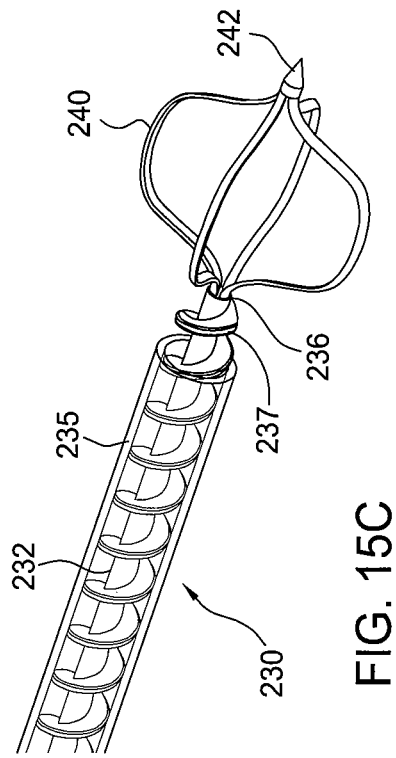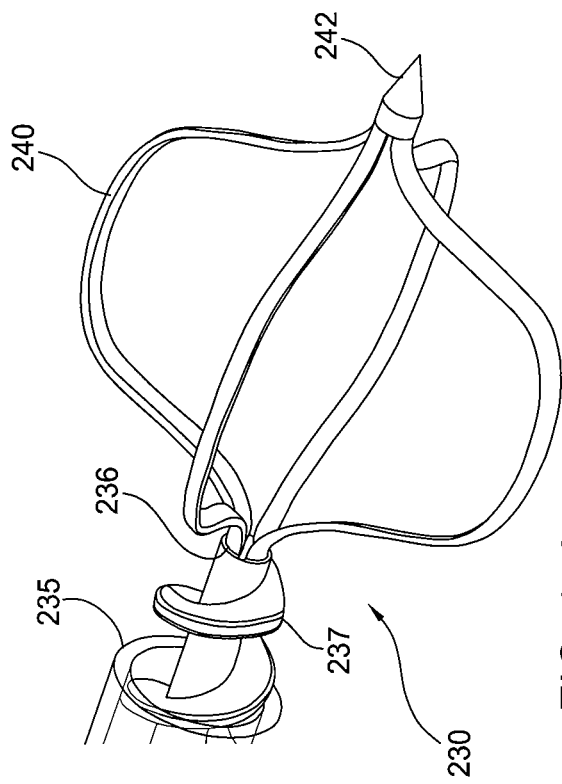
FIG. 15B
FIG. 15C
FIG. 15A

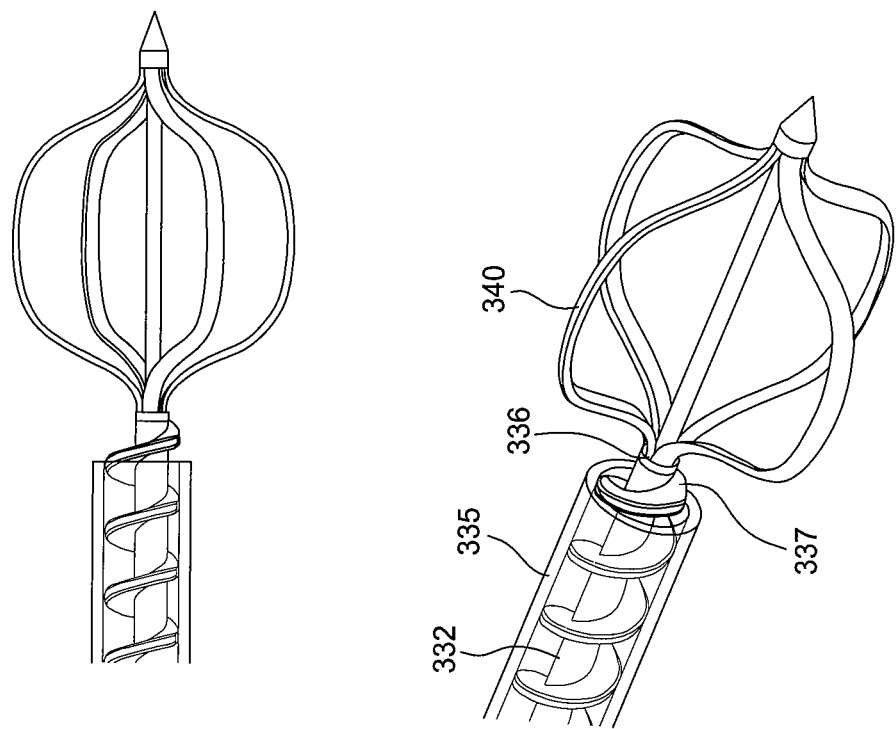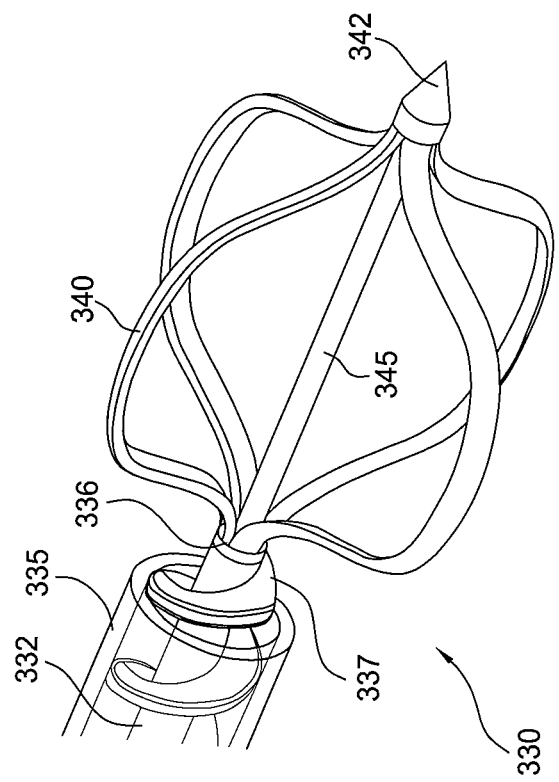
FIG. 17A

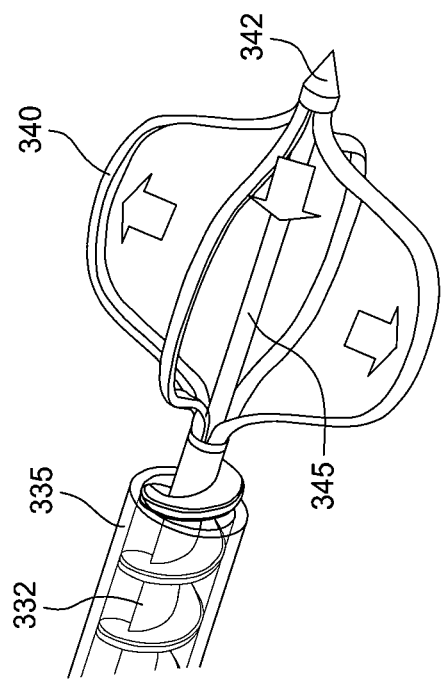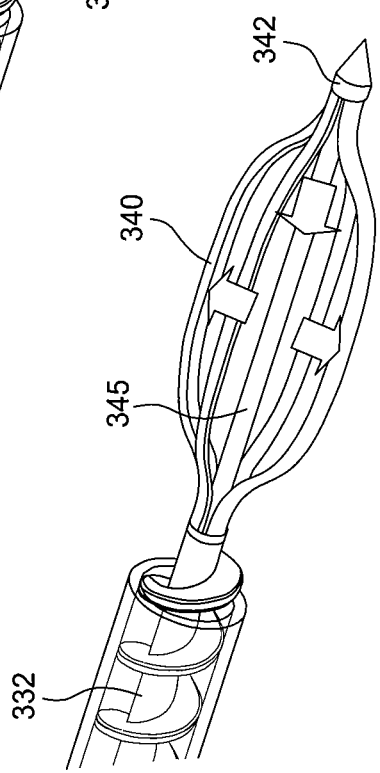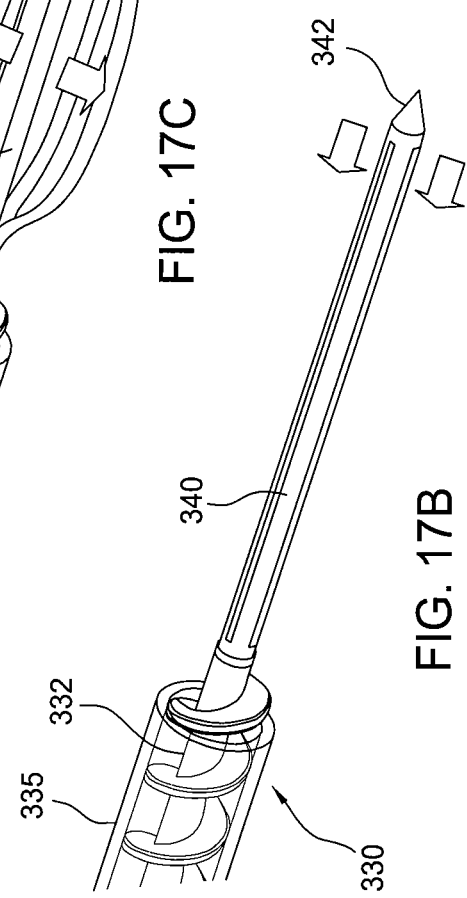

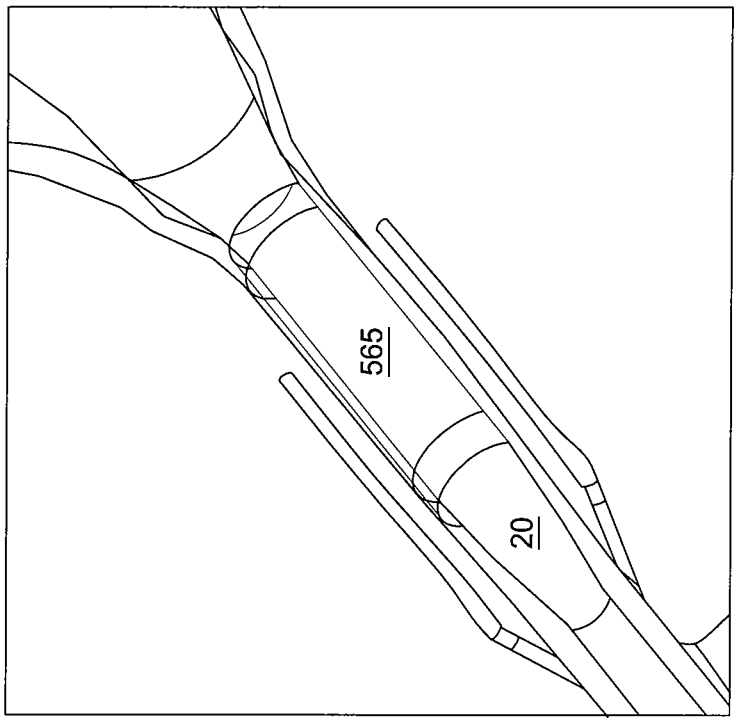
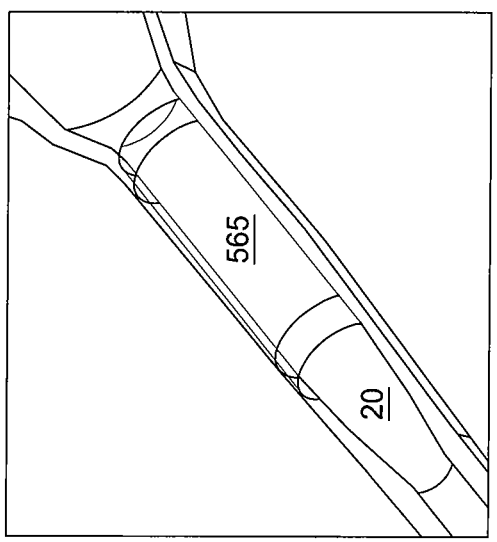
FIG. 23

APPARATUS AND METHOD FOR PROSTATIC TISSUE REMOVAL

CROSS-REFERENCE TO RELATED APPLICATIONS

This application claims benefit of U.S. Provisional Patent Application Ser. No. 60/883,686, filed on Jan. 5, 2007, which application is incorporated herein by reference in its entirety.

BACKGROUND OF THE INVENTION

1. Field of the Invention

Embodiments of the present invention generally relate to methods and apparatus for destroying tissues in the body. Particularly, embodiments of the present invention generally relate to methods and apparatus for removing prostatic tissue. More particularly, embodiments of the present invention generally relate methods and apparatus for surgical enlargement of the urethra lumen with minimal while conserving the natural inner lining of the urethra.

2. Description of the Related Art

Benign prostatic hyperplasia ("BPH") is a common medical condition experienced by men over 50 years old. BPH arises from the benign replication and growth of cells in the prostate. Hyperplastic enlargement of the prostate gland often leads to compression of the urethra, resulting in obstruction of the urinary tract and the subsequent development of symptoms including frequent urination, decrease in urinary flow, pain, discomfort, and dribbling.

Traditional treatments of BPH include non-surgical and surgical treatments. Treatment with medication is usually recommended for mild cases of BPH. For more severe cases, surgery to resect the prostate is usually performed. Transurethral resection of the prostate ("TURP") is commonly performed to remove a large portion of the prostate. In order to enlarge the diameter of the urethra, TURP removes the inner lining of the urethra and the surrounding prostatic tissue. Due the procedure's aggressive nature, one drawback of TURP is that too much tissue is removed, thereby causing cavitation. Another drawback is that substantial bleeding may occur from destruction of the inner lining, thereby causing formation of blood clots.

Laser surgery is another common procedure performed to remove portions of the prostate. Although laser surgery causes less bleeding, it delivers light energy to the prostatic tissue by burning through the inner lining of the urethra. Another disadvantage of laser surgery is that it may not efficiently remove the desired volume of resection. For example, a typical laser may have a 1 mm diameter. In order to make a 1 cm diameter cut, a substantial number of laser fires must be executed.

There is a need, therefore, for methods and apparatus for removing prostatic tissue with minimal damage to the inner lining of the urethra.

SUMMARY OF THE INVENTION

Embodiments of the present invention generally relates to methods and devices for treating prostatic tissues. In one embodiment, a method of treatment includes removing prostatic tissues adjacent the urethra and enlarging the lumen of the urethra, whereby the treatment conserves a natural wall of the urethra.

In another embodiment, a method of removing tissue of a prostate proximate a urethra having an inner lining. The method includes positioning a catheter in the urethra; inserting a mechanical debrider through the catheter; positioning the mechanical debrider in the prostate proximate the tissue to be removed; rotating the mechanical debrider against the tissue; and removing the prostatic tissue, thereby forming a cavity adjacent the inner lining of the urethra.

In another embodiment, a medical device includes a catheter having a first channel and a second channel; a first medical tool positioned in the first channel; and a mechanical debrider positioned in the second channel, wherein the debrider includes an outer tube and a tissue removal member.

In yet another embodiment, a medical device includes a catheter; an endoscope positioned in the catheter; and a mechanical debrider extending out of the catheter, wherein the debrider includes an outer tube and a tissue removal member.

Embodiments of medical devices and treatment method disclose herein are particularly useful for treating benign prostate hyperplasia (BPH). However, it must be noted that the devices and treatment methods are suitable to remove other tissues such as tumor cells and cancer cells. Moreover, it is further contemplated that the devices and treatment methods may be used to treat other bodily tissues and is not limited to the prostate.

BRIEF DESCRIPTION OF THE DRAWINGS

So that the manner in which the above recited features of the present invention can be understood in detail, a more particular description of the invention, briefly summarized above, may be had by reference to embodiments, some of which are illustrated in the appended drawings. It is to be noted, however, that the appended drawings illustrate only typical embodiments of this invention and are therefore not to be considered limiting of its scope, for the invention may admit to other equally effective embodiments.

FIGS. 1 and 1A illustrate an enlarged prostate constricting the urethra.

As shown in FIGS. 4 and 4A, a guide needle extends out of a side port of a catheter of the surgical device. FIG. 4B illustrates another embodiment wherein the guide needle extends out of the front end of the catheter.

FIGS. 6A-E illustrate operation of the surgical device. FIGS. 6A-B illustrates operation of the removal device. FIGS. 6C-E illustrate a multi-step process of forming a cavity.

FIGS. 11A-C illustrate the process of positioning a stent in the lumen.

FIGS. 13A-B illustrate views of the lumen of the urethra before and after the surgical procedure.

FIGS. 15A-E illustrate views of another embodiment of a debrider.

FIGS. 17A-D illustrate views of another embodiment of a debrider. FIGS. 17B-D illustrate the expansion process of the blades of the debrider shown in FIG. 17A.

FIG. 23 illustrates a stent positioned in a lumen.

DETAILED DESCRIPTION

FIG. 1 shows an enlarged prostate 10 constricting the lumen 20 of the urethra 15. The prostate 10 attaches near the bladder neck, and the urethra 15 extends from the bladder 25 and through the prostate 10. FIG. 1A is an exploded view of the constricted urethra 15.

Figure 2A:
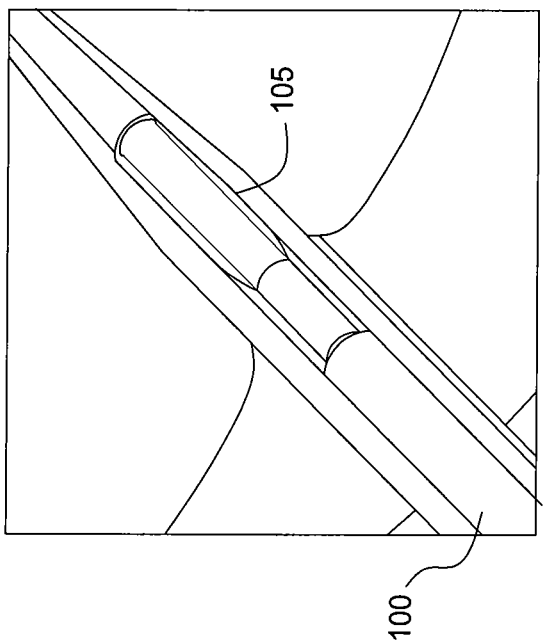
FIGS. 2 and 2A illustrate a surgical device inserted into the urethra according to one embodiment.
Figure 2:
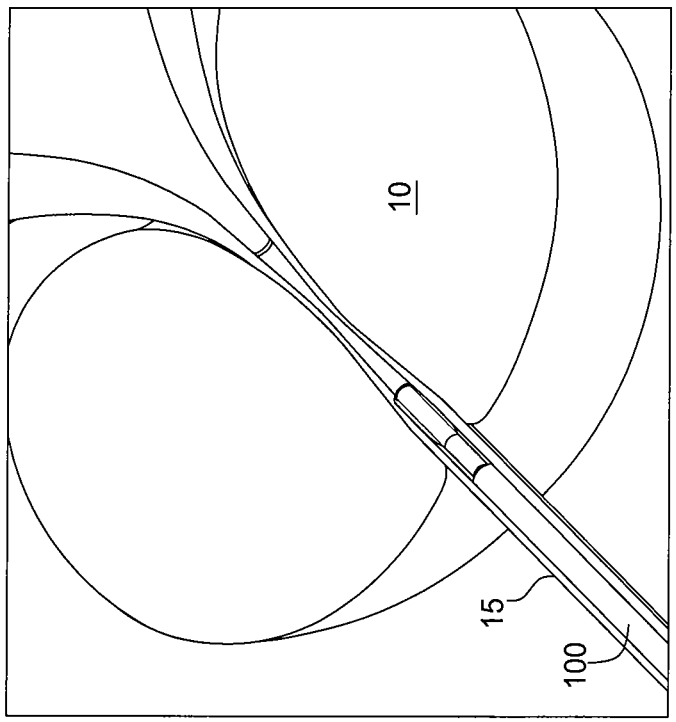

Embodiments of the present invention provide methods and apparatus for removal of prostatic tissue to alleviate the constriction on the urethra 15. In one embodiment, the method begins with inserting a surgical device 100 into the urethra 15 and positioning the surgical device 100 at a desired location, see step 1 as illustrated in FIGS. 2 and 2A. The surgical device 100 includes an expandable member such as an inflatable balloon 105 fitted to the outer surface of the front end of the device 100. The balloon 105 may be inflated using a fluid such as air, water, and combinations thereof. The balloon 100 may be made from polyurethane or other suitable expandable material. The balloon 100 may be inflated to facilitate the exchange, insertion, or removal of a probe or other tools. In this respect, the balloon 100 may act as a dilator to expand the urethra 15 to the desired diameter.

Figure 3:
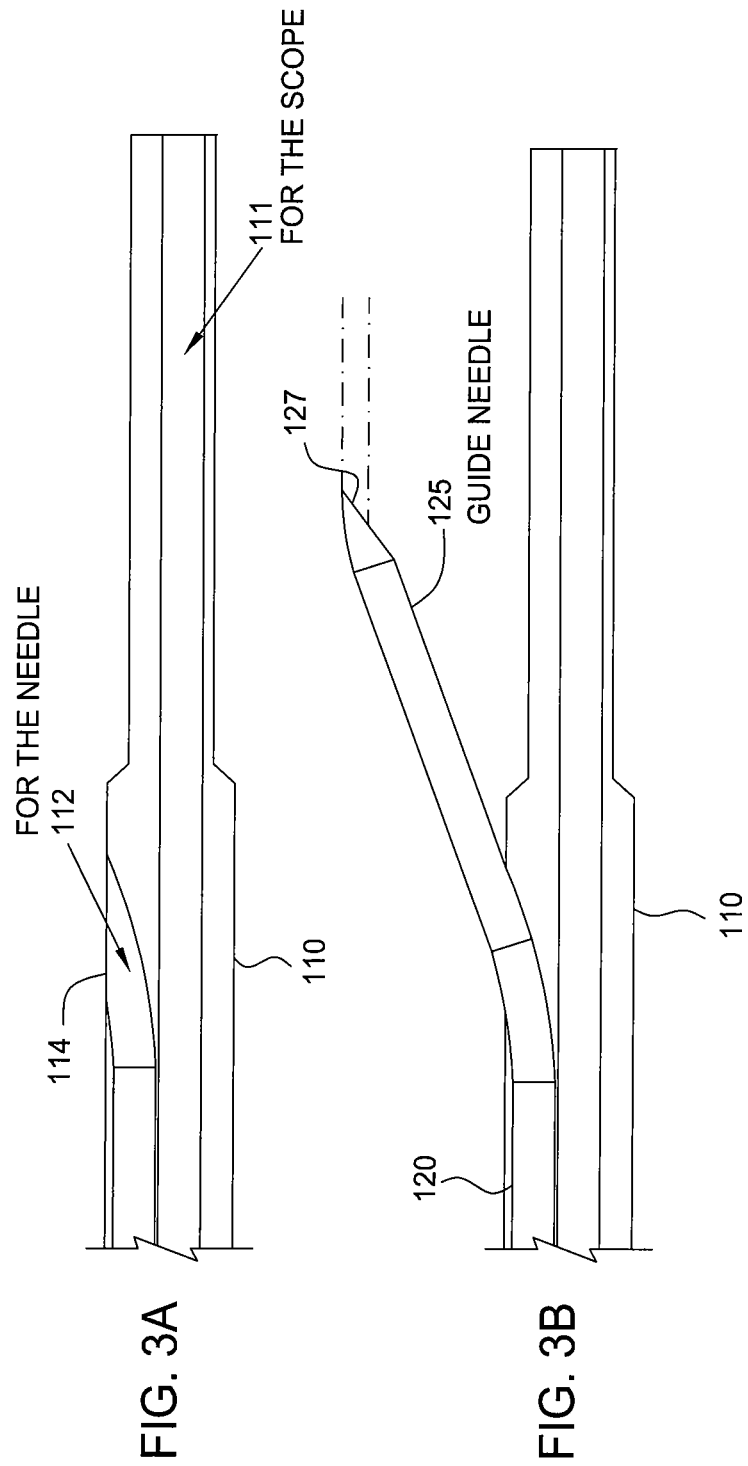
FIGS. 3A-B illustrate an embodiment of the surgical device.

Referring now to FIGS. 3A and 3B, the surgical device 100 includes a catheter 110 having at least two channels 111, 112. A first channel 111 may be a central channel extending through the front end of the catheter 110. The central channel 111 may be used to deliver a tool such as an endoscope. The endoscope may be used for visualization during the procedure. A second channel 112 in the catheter 110 exits the catheter through a side port 114. The second channel 112 may be used to deliver a tool such as a cannula 120. In one embodiment, the cannula 120 is fitted with a guide needle 125 for insertion into the prostatic tissue. Suitable materials for the guide needle 125 include a flexible memory metal. As shown, the tip 127 of the guide needle 125 may be angled to direct a tool, such as a debrider, in the desired direction when it leaves the guide needle 125. The degree of the angle may be any desired angle such that the tool may be advanced in the proper direction. For example, the tip 127 may have an angle such that the debrider may turn sufficiently after leaving the cannula 120 and proceed in a direction substantially parallel to the catheter 110. FIG. 3A shows the guide needle 125 retracted in the second channel 112. FIG. 3B shows the guide needle 125 in the advanced position. In another embodiment, the cannula 120 may be rotatable. In this respect, the angle of departure of the debrider may be controlled and adjusted. In yet another embodiment, the needle tip 127 may be straight for a straightforward advancement in the prostate 10. In yet another embodiment, the second channel 112 in the catheter 110 may be angled such that the guide needle 125 is already positioned in the proper direction when it exits the catheter 110. It must be noted that additional channels (central or side channels) may be provided in the catheter to accommodate additional tools or other requirements. For example, one or more channels may be used to deliver a fluid to operate a tool.

Figure 4:
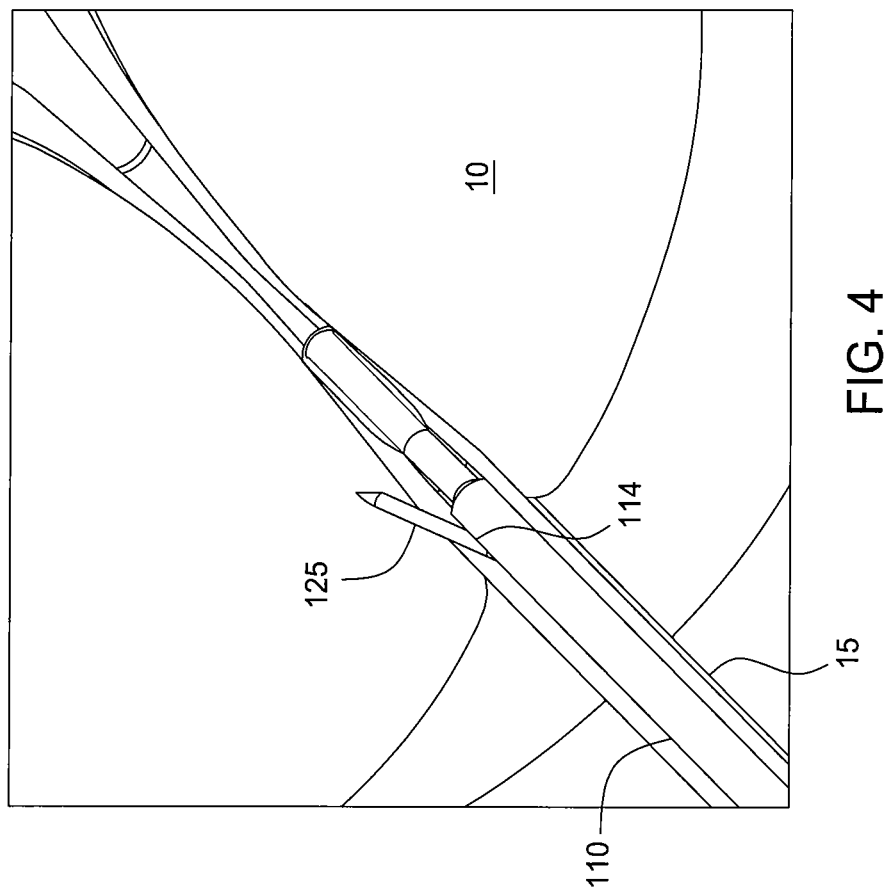
FIGS. 4 and 4A-B illustrate operation of the surgical device.
Figure 4A:
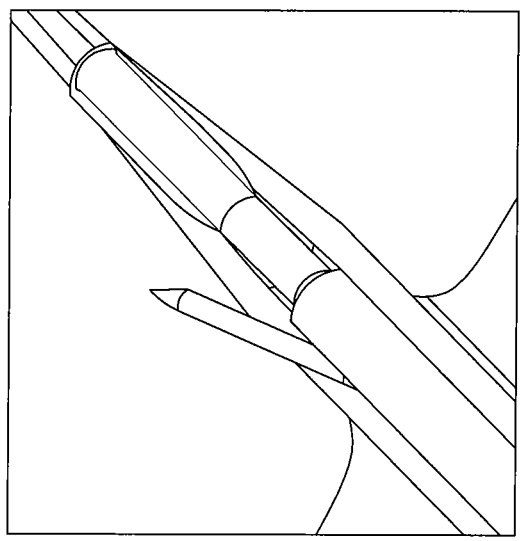
Figure 4B:
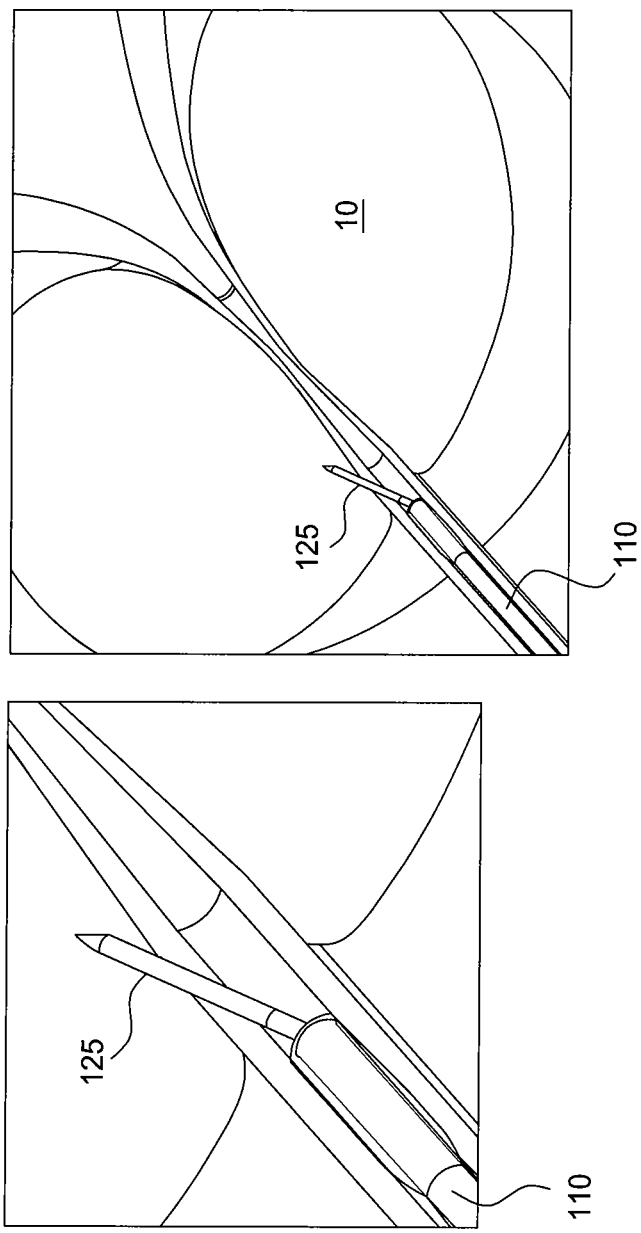

Step 2 of the procedure includes advancing the guide needle 125 through the side port 112 and at least partially into the prostatic tissue, as illustrated in FIGS. 4 and 4A. It can be seen that the guide needle 125 only creates a small hole in the urethral wall. The cannula 120 and the guide needle 125 are now in position to deliver another tool. In another embodiment, the guide needle 125 may exit the catheter 110 through the front end, as illustrated in FIG. 4B. The guide needle 125 may be inserted through a second central channel adjacent the central channel 111 housing the endoscope, or the central channel housing the endoscope after the endoscope is retrieved.

Figure 5:
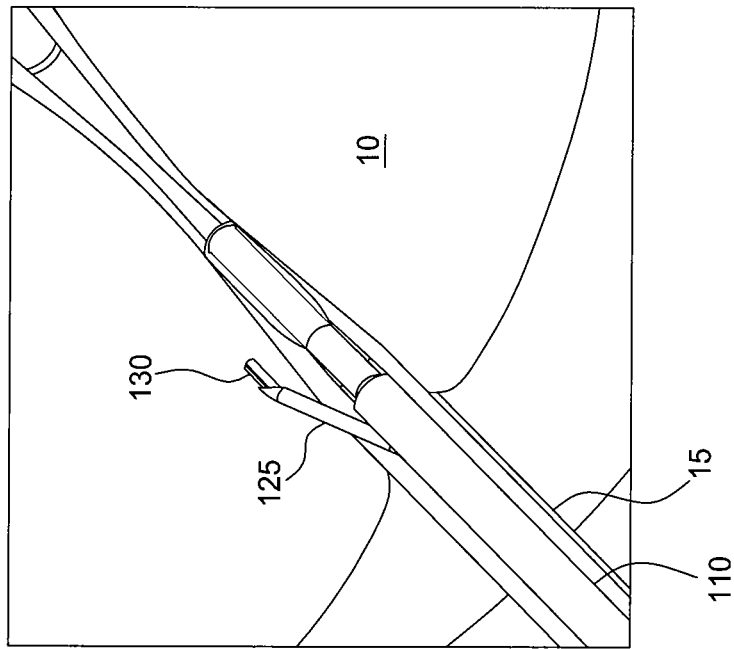
FIGS. 5 and 5A illustrate operation of the surgical device. As shown, a removal device is inserted through the cannula.
Figure 5A:
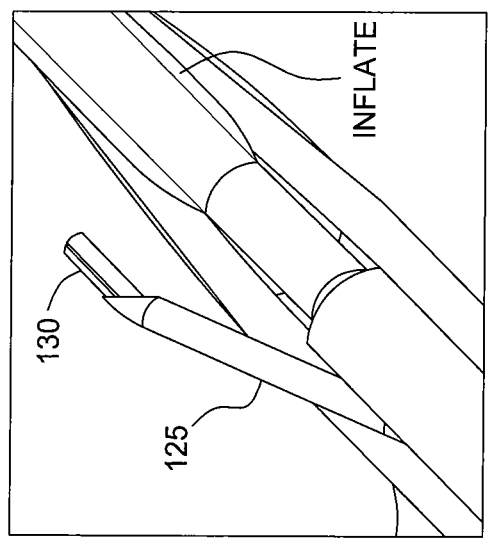

In Step 3, a debrider 130 is inserted through the guide needle 125 and into the prostatic tissue 10, as illustrated in FIGS. 5 and 5A. The direction of the debrider's movement is dictated by the angle of the tip 127 of the guide needle 125. The distance of travel of the debrider 130 may be controlled by an operator at the other end of the catheter 110. In one embodiment, the debrider 130 is a mechanical debrider that is operated to remove prostatic tissue in its path. Other suitable debriders include, but not limited to, laser, RF catheter probe, mechanical aspirator, microwave probe, and combinations thereof.

In step 4, the debrider 130 is actuated to remove portions of the prostatic tissue. Referring now to FIGS. 6A-B, an embodiment of the debrider 130 includes a longitudinal body 132 disposed inside an outer tube 135. The longitudinal body 132 may have an auger portion 137 disposed on an outer surface and a removal member such as a blade 140 that is slidable in the outer tube 135. The debrider 130 may be equipped with one or more blades 140. To actuate the debrider 130, the tube 135 is initially inserted through the guide needle 125 to a desired distance. Thereafter, the blade 140 and the auger portion 137 are extended out of the outer tube 135. The longitudinal body 132 is then rotated to apply torque to the blade 140 and the auger portion 137. Rotation and advancement of the free end of the blade 140 removes prostatic tissue in its path of rotation to form a cavity 150. In this respect, the debrider 130 may be operated to remove portions of the prostatic tissue adjacent the urethra 15. The blade 140 may be advanced to any distance to form the desired cavity size 150. During operation, a groove in the auger portion 137 pulls some of the loosened tissue into the outer tube 135 for removal. Additionally or alternatively, the longitudinal body 132 may be reciprocated back and forth to remove the loosened tissue. In another embodiment, the guide needle 125 may be provided with aspiration and/or suction to facilitate tissue removal.

In one embodiment, the balloon 105 is inflated during the operation of the debrider 130. Expansion of the balloon 105 forces additional prostatic tissue toward the debrider 130 and into the path of rotating blade 140, see FIGS. 6A-B. In this respect, maximum tissue removal may be achieved because some of the prostatic tissue that would not have been in the path of the rotating blade 140 may now be removed.

Figure 6E:
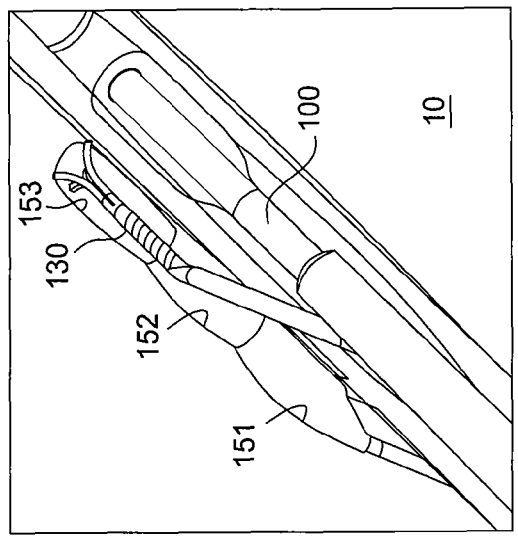
Figure 6D:
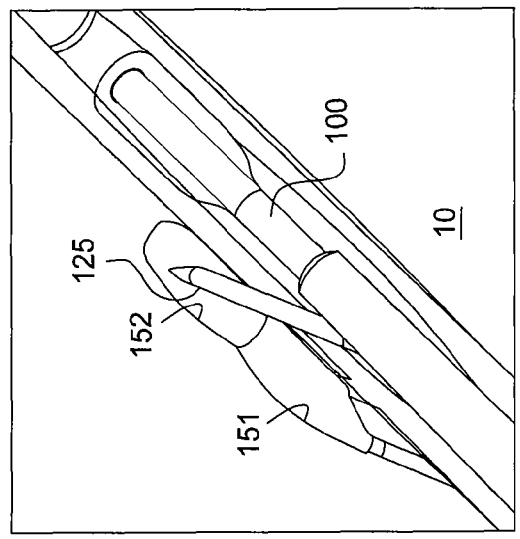
Figure 6C:
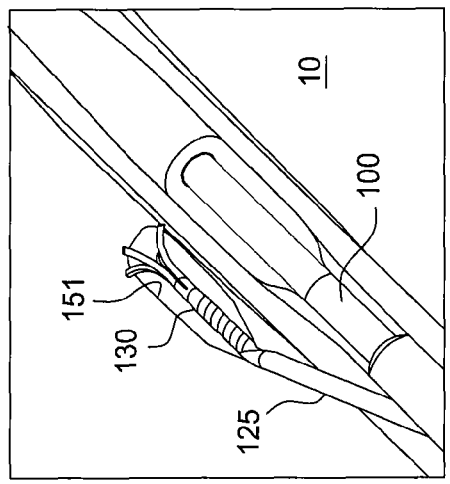

In another embodiment, the prostatic tissue may be removed in multi-step fashion. Referring now to FIGS. 6C-E, the debrider 130 is initially used to form a small cavity 151 in the prostate 10. Then, the debrider 130 and the guide needle 125 are retrieved. The surgical device 100 is advanced a short distance such that the successive cavity 152 will overlap with the previous cavity 151. The guide needle 125 is then inserted through the urethral wall followed by the debrider 130. The second cavity 152 is then formed. Thereafter, the guide needle 125 and the debrider 130 are retrieved. This process may be repeated until the desired length of cavity is formed, for example, to form a third cavity 153.

Figure 7:
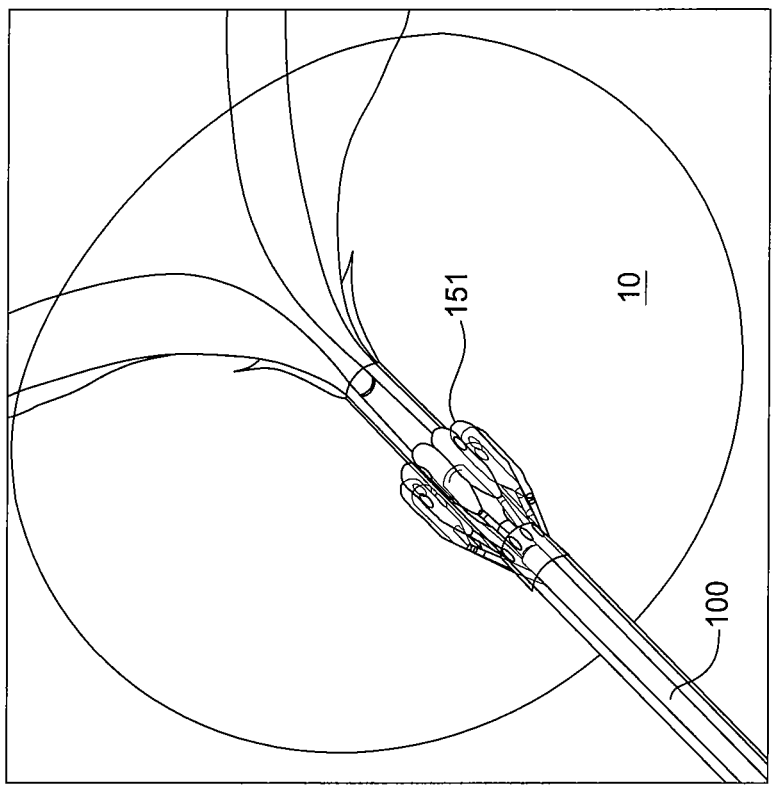
FIGS. 7 and 7A-B illustrate removal of tissue around the urethra.
Figure 7A:
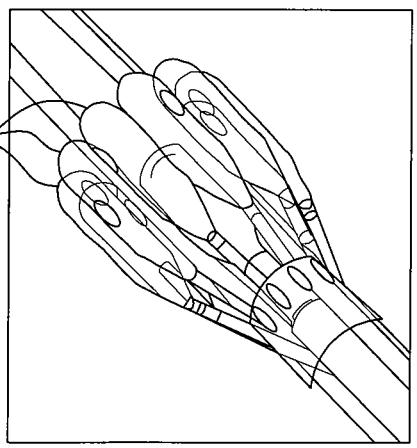
Figure 7B:
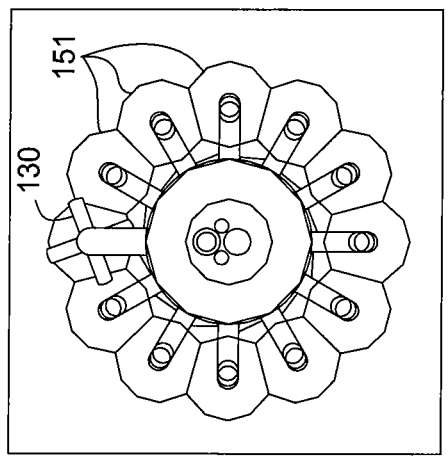

At step 5, the surgical device 100 may be used to form one or more cavities 151 adjacent the urethra 15. FIG. 7 shows one embodiment of multiple tubular cavities 151 formed around the urethra 15. FIG. 7A is a close up view of the tubular cavities 151. FIG. 7B is a cross-sectional view of FIG. 7 taken at the urethra 15. Although the Figures show the tubular cavities 151 are positioned circumferentially, it must be noted that any suitable number or combination of tubular cavities may be formed. For example, tubular cavities 151 may be formed at 0, 90, 180, and 270 degrees around the urethra 15. In another example, two or more tubular cavities 151 may be spaced circumferentially around the urethra 15.

Figure 8:
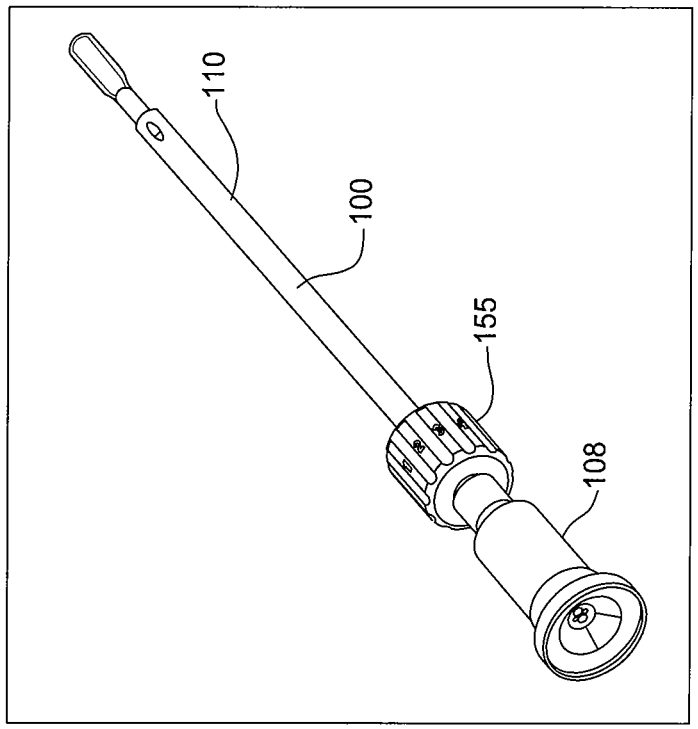
FIGS. 8 and 8A illustrate an embodiment of a rotation controller.
Figure 8A:
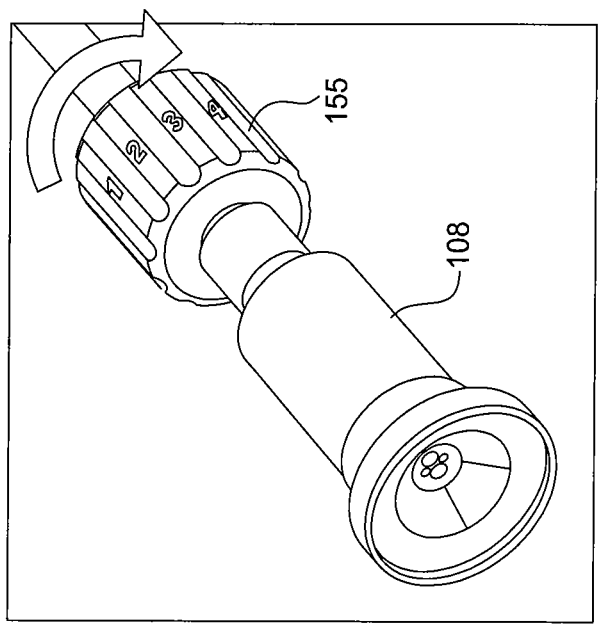

FIGS. 8 and 8A show the control end 108 of the surgical device 100. In one embodiment, the control end 108 is equipped with a rotation controller 155 adapted to rotate the catheter 100 to the proper position for insertion of the guide needle 125 into the prostate 10. The controller 155 may be marked with numbers to indicate the angle of rotation. The rotation controller 155 may be used to facilitate formation of one or more tubular cavities 151 around the urethra 15.

Figure 9A:
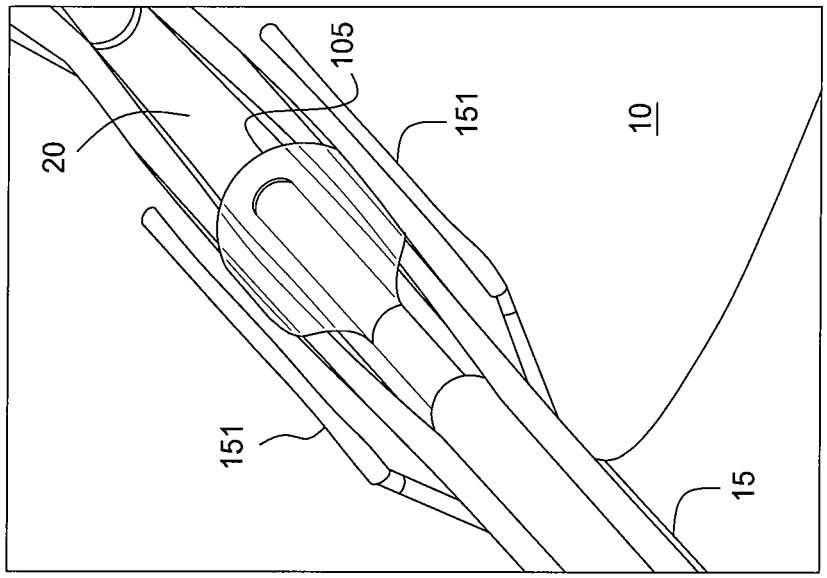
FIGS. 9A-C illustrate inflation of a balloon in the lumen.
Figure 9B:
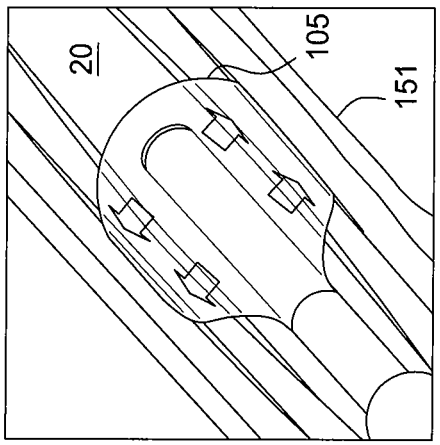
Figure 9C:
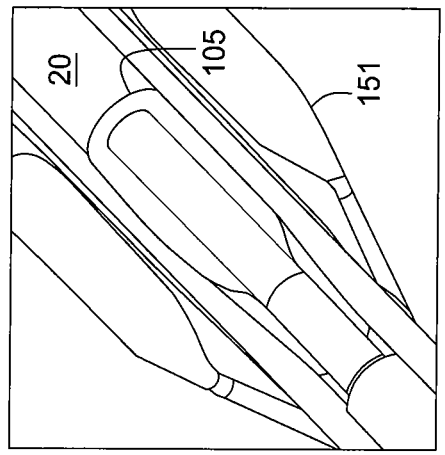

After the desired quantity of prostatic tissue has been removed, the guide needle 125 and the debrider 130 are retracted back into the side passage 112. At step 6, the balloon 105 is then inflated to enlarge the lumen 20 of the urethra 15. This process is shown in FIGS. 9A-C. The inflated balloon 105 helps to maintain the urethra 15 in a dilated state. During debriding of the prostatic tissue, bleeding may occur within that cavity 151. One added benefit of the balloon inflation is that the balloon 105 may tamponage the bleeding. Thus, one embodiment of the present invention includes inflating a balloon 105 to tamponage bleeding.

Figure 10A:
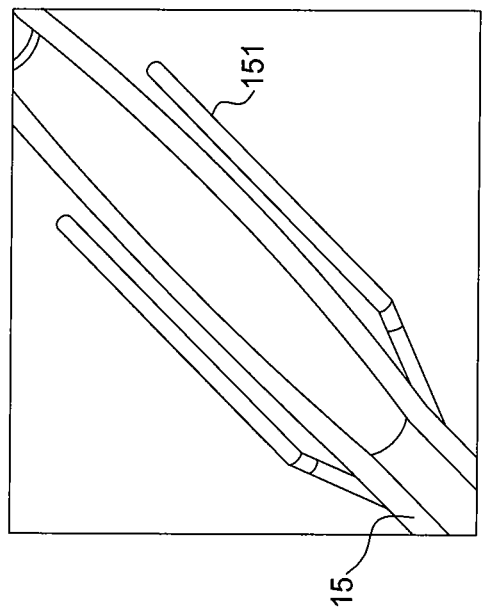
FIGS. 10 and 10A illustrate enlargement of the lumen after the procedure.
Figure 10:
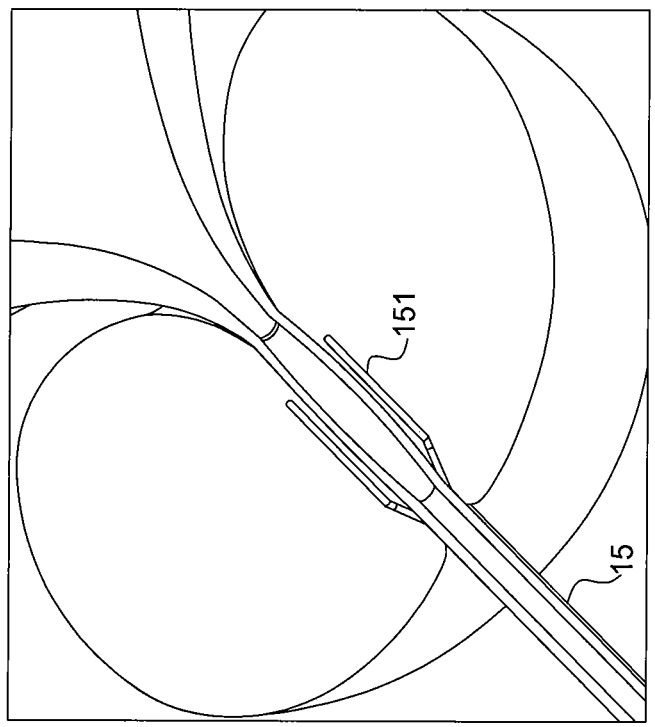

At step 7, the surgical device 100 is removed from the urethra 15, as illustrated in FIGS. 10 and 10A. It can be seen now that the constricted portion of the urethra 15 has been enlarged and dilated. Additionally, because the cavities 151 are formed adjacent the urethra 15, the procedure preserved the inner lining of the urethra 15. Further, the cavities 151 reduce the compression pressure from the prostate 10 previously acting on the urethra 15 to help maintain the lumen 20 of the urethra 15 in the enlarged state.

Figure 12A:
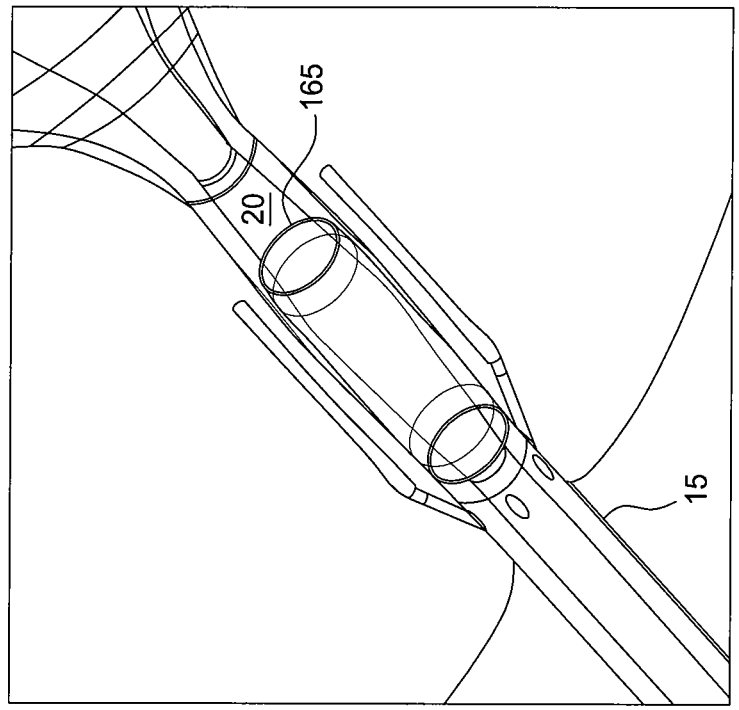
FIGS. 12A-C illustrate different views of a polyethylene urethral stent.
Figure 12B:
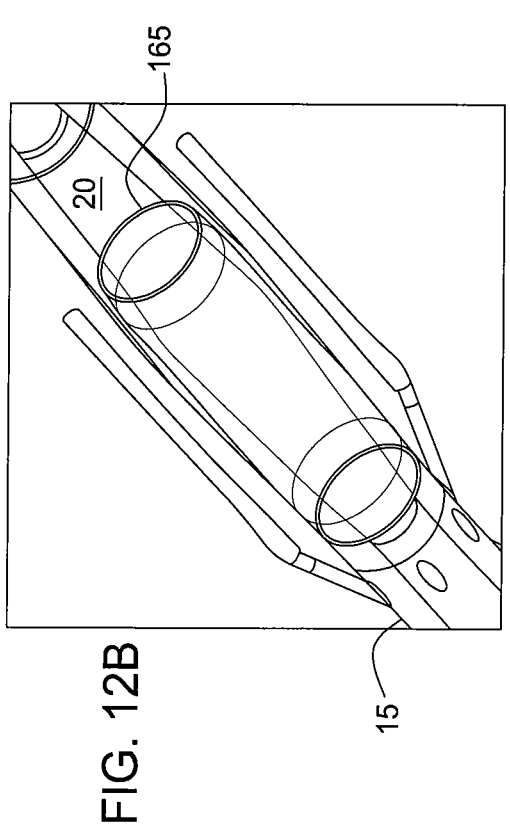
Figure 12C:
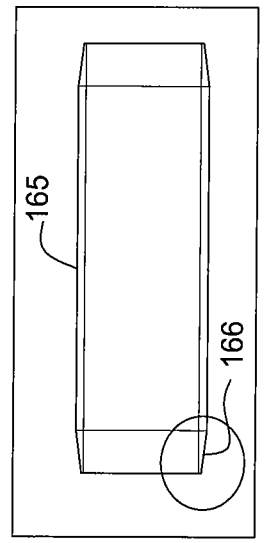

In another embodiment, an optional urethral stent 160 may be installed in the urethra 15 to maintain the dilated state. Potential bleeding caused by the debrider 130 may push the enlarged portion of the lumen 20 back, thereby constricting it. The urethral stent 160 may be temporarily installed to prevent the enlarged lumen 20 from constriction by the bleeding. An exemplary stent suitable for use is a mesh tube. In FIG. 11A, the urethral stent 160 is positioned around the front end of the surgical device 100 and the balloon 105 for insertion into the urethra 15. Thereafter, the balloon 105 is inflated to expand the urethral stent 160 against the inner wall of the urethra 15, as shown in FIG. 11B. After expansion, the balloon 105 is deflated and the surgical device 100 is removed, leaving behind the expanded urethral stent 160, as shown in FIG. 11C. In one embodiment, the temporary stent 160 may be installed for 1-14 days; preferably, about 2-8 days; more preferably, 3-5 days. The stent 160 may be expanded to a size that is larger than the constricted diameter. Other suitable stents include nitinol stents and polyethylene urethral stent. FIGS. 12A-B show the polyethylene urethral stent 165 positioned in the enlarged lumen 20 of the urethra 15. FIG. 12C shows a close up view of the polyethylene urethral stent 165. In one embodiment, the polyethylene urethral stent 165 has tapered ends 166 to facilitate insertion or removal.

FIGS. 13A-B illustrate the prostate 10 before and after the surgical procedure. It can be seen in FIG. 13B that the surgical procedure according to one embodiment has enlarged the lumen 20 of the urethra 15 while conserving the natural wall 22 of the urethra 15.

Figure 14B:
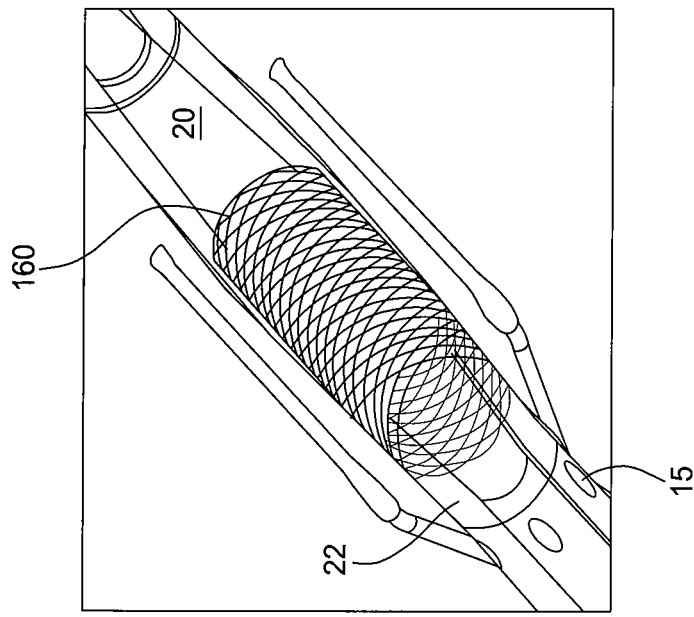
FIGS. 14A-B illustrate views of the lumen of the urethra before and after the surgical procedure with placement of a stent.
Figure 14A:
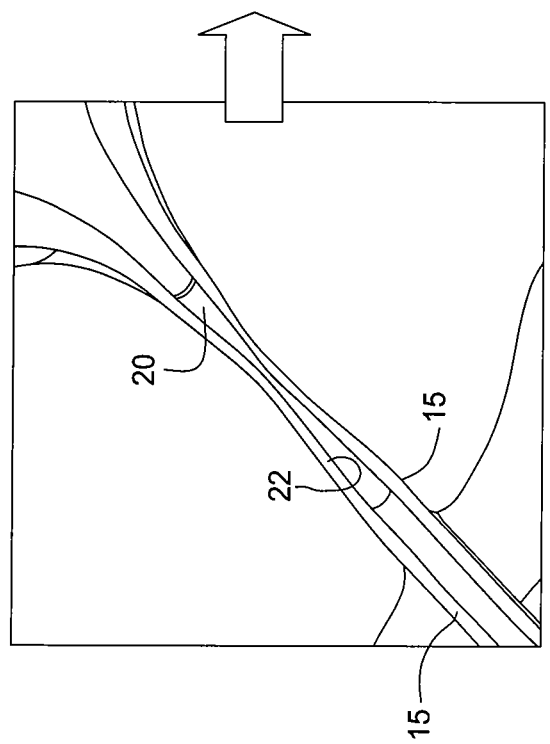
Figure 15E:
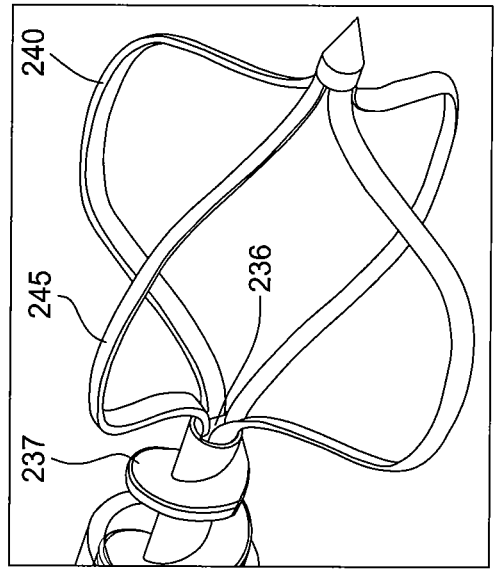
Figure 15D:
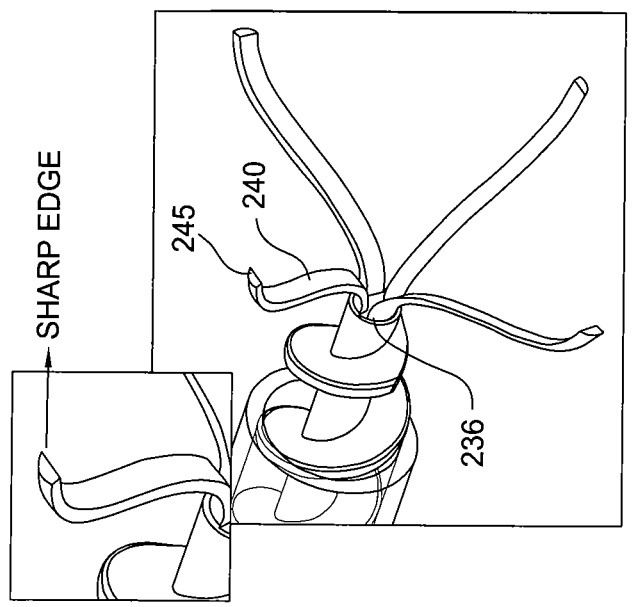

FIGS. 14A-B illustrate the prostate 10 before and after the surgical procedure according to another embodiment. It can be seen in FIG. 14B that the surgical procedure has successfully enlarged the lumen 22, installed a stent 160, and conserved the natural wall 22 of the urethra 15.

Figure 16A:
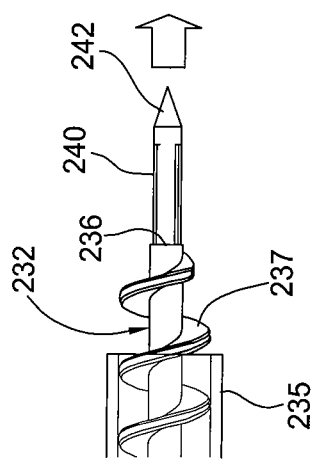
FIGS. 16A-C illustrate the expansion process of the blades of the debrider shown in FIGS. 15A-E.
Figure 16B:
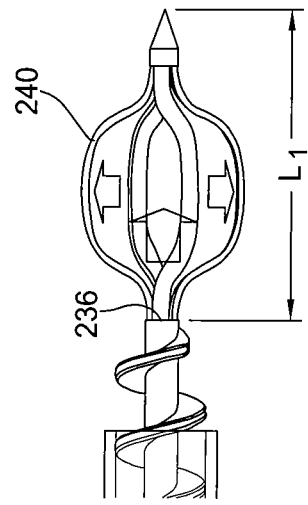
Figure 16C:
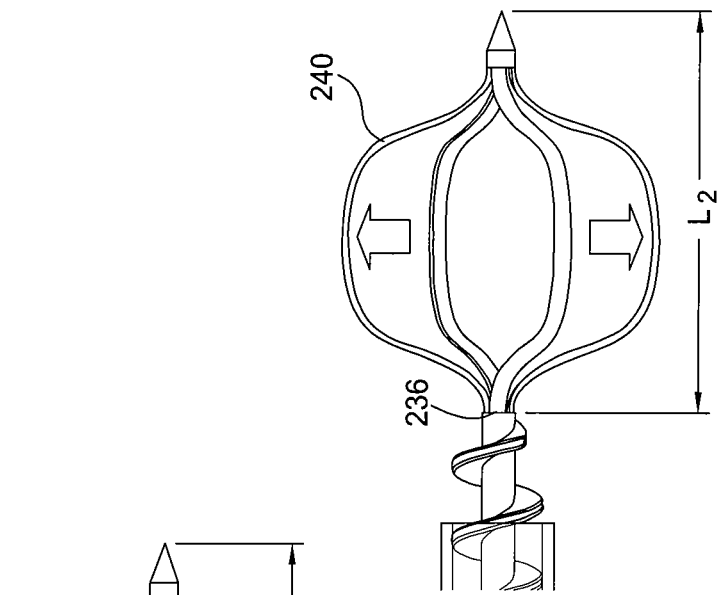

FIGS. 15A-E illustrate another embodiment of a mechanical debrider 230. The debrider 230 includes a longitudinal body 232 movably disposed within an outer tube 235. The outer tube 235 may be inserted through the cannula 120 and the guide needle 125. The longitudinal body 232 includes a passage 236 extending therethrough and an auger shaped outer portion 237. A removal member such as a blade 240 may be inserted through the passage 236 of the longitudinal body 232. As shown, the removal member includes four blades 240 connected at the front end using a pointed tip 242. As shown in the cross-sectional view of FIG. 15D, at least one angle edge 245 may be formed on one side of the blade 240 for cutting through the tissue. The blades 240 may be manufactured from flexible memory metal. The blades 240 are adapted to flex radially outward after exiting the passage 236. As shown in FIGS. 16A-C, the diameter of the removal member 240 may be adjusted to control the volume of tissue cavity to be created. In one embodiment, the diameter of the removal member 240 is determined by the length of the blades 240 extending beyond the passage 236. In FIG. 16B, a short blade extension $L_1$ expands the removal member 240 to a small diameter. In FIG. 16C, a longer extension $L_2$ expands the removal member 240 to a larger diameter. During operation, the diameter of the removal member 240 may be increased in a stepwise fashion to gradually increase the size of the tissue cavity, or the diameter of the removal member 240 may be constant and the removal member is advanced forward to increase the size of the tissue cavity, or combinations thereof.

FIGS. 17A-D show another embodiment of a mechanical debrider 330. The debrider 330 includes a longitudinal body 332 movably disposed within an outer tube 335. The outer tube 335 may be inserted through the cannula 120 and the guide needle 125. The longitudinal body 332 includes a passage 336 extending therethrough and an auger shaped outer portion 337. The removal member includes four blades 340 connected to the longitudinal body 332 at one end and the pointed tip 342 at another end. A cable 345 extending through the passage 336 is inserted between the blades 340 and connected to the pointed tip 342. The diameter of the removal member 340 may be adjusted by extending or retracting the cable 345. In FIG. 17B, the entire length of the blades 340 is extended beyond the outer tube 335. To expand the removal member 340, the cable 345 is retracted relative to the longitudinal body 332 to pull the pointed tip 342 towards the outer tube 335 is shown in FIG. 17C. The retraction causes the blades 340 to expand radially. As shown in FIG. 17D, when more cable 345 is retracted, the expansion increases. Thus, the diameter of the removal member 340 may be controlled by controlling the extent of the cable 345 retraction. In another embodiment, a shaft or other conveying member may be used instead of a cable to control the expansion.

Figure 18:
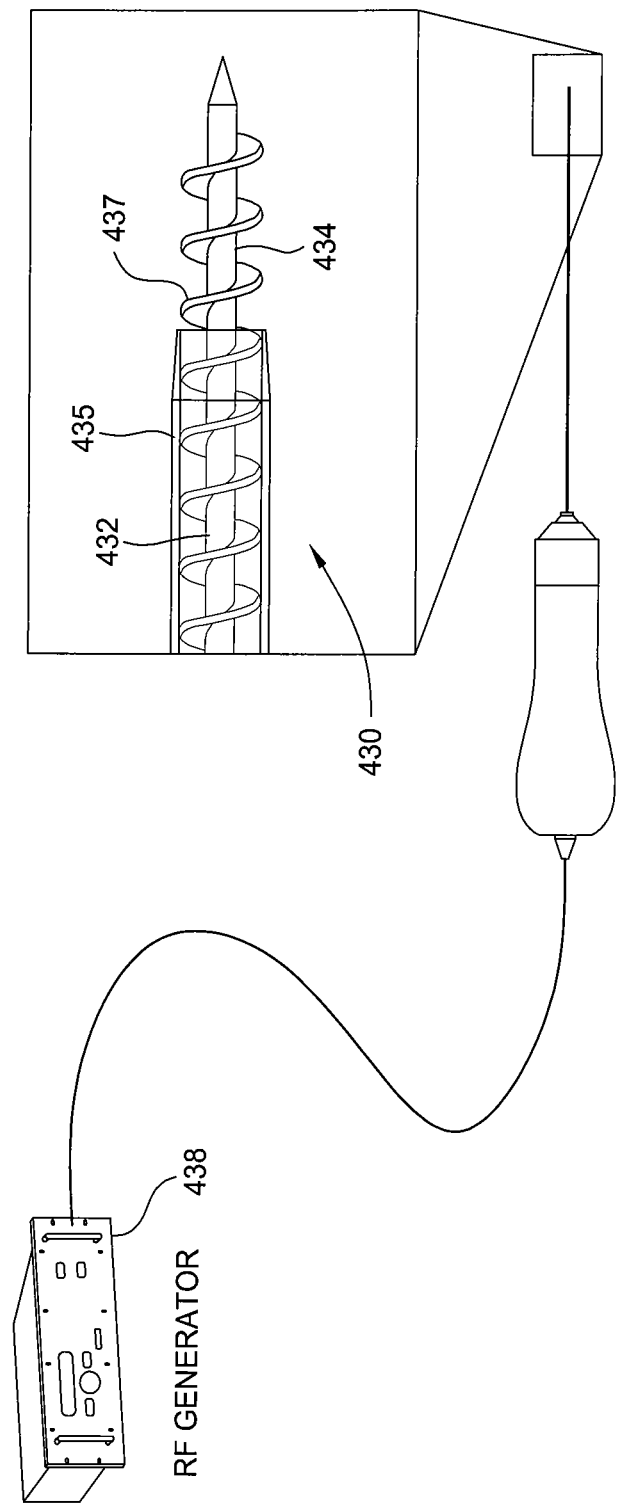
FIG. 18 illustrates an embodiment of a debrider with a built in RF probe.
Figure 19:
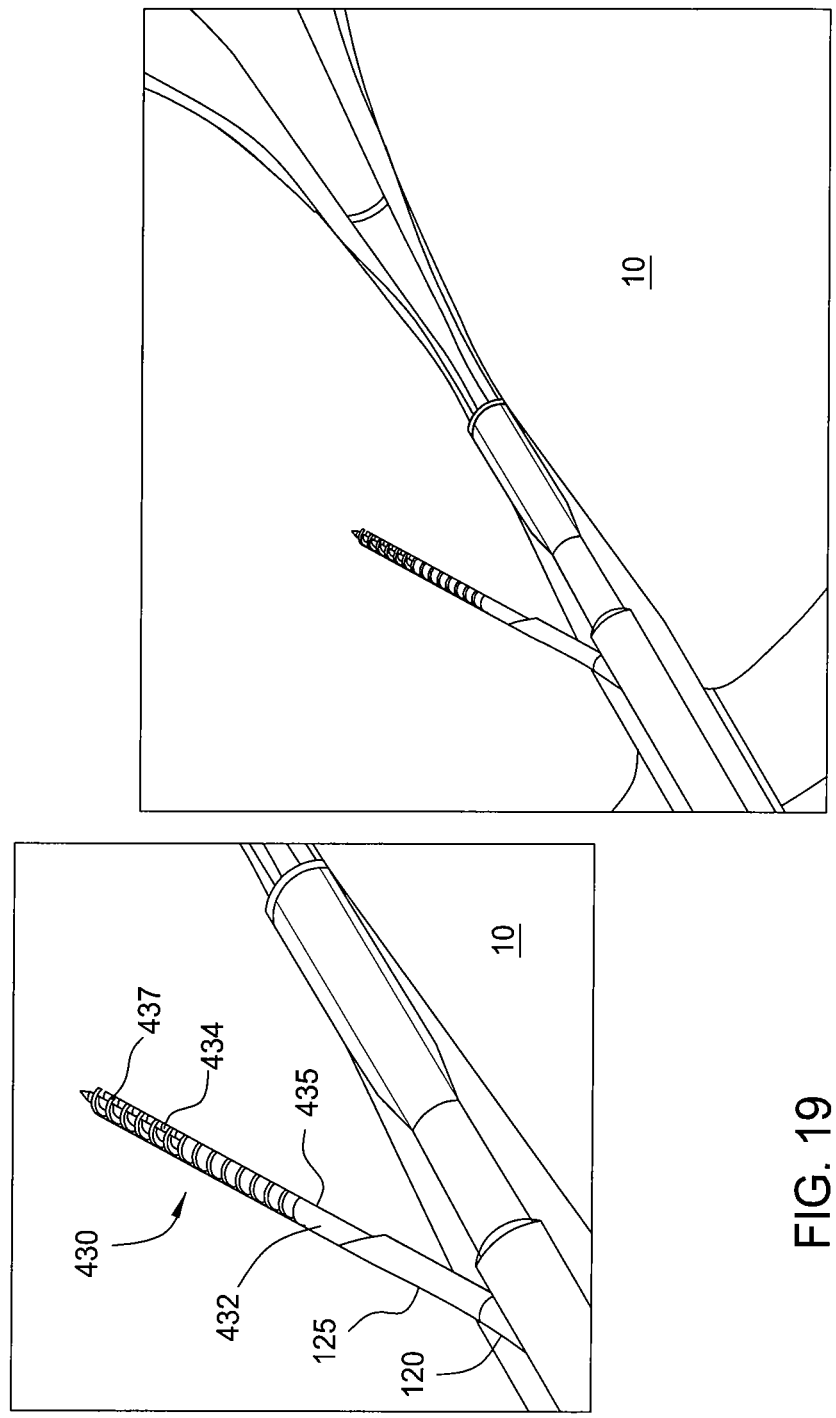
FIGS. 19, 20, 21A-B illustrate operation of the debrider of FIG. 18.
Figure 20:
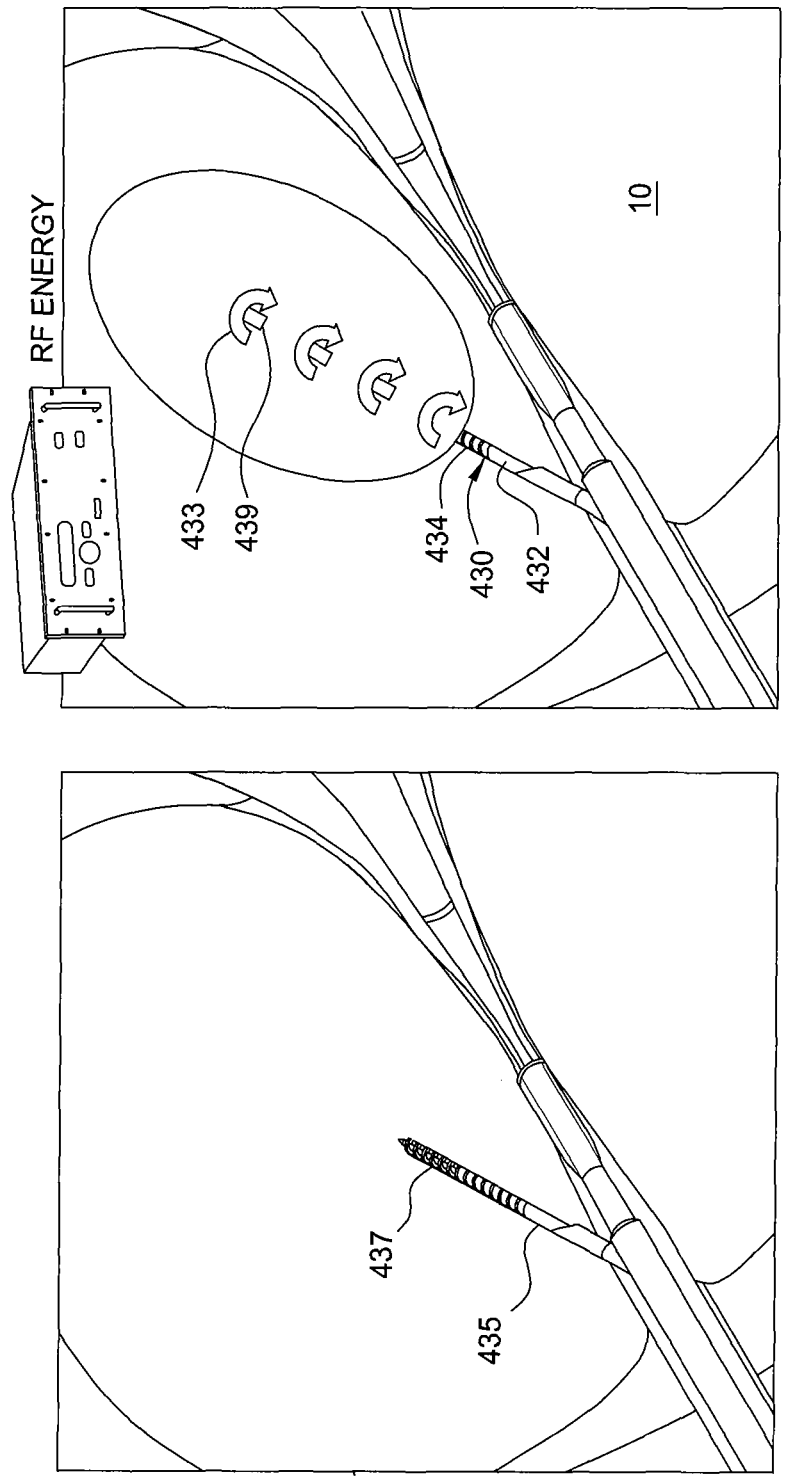
Figure 21B:
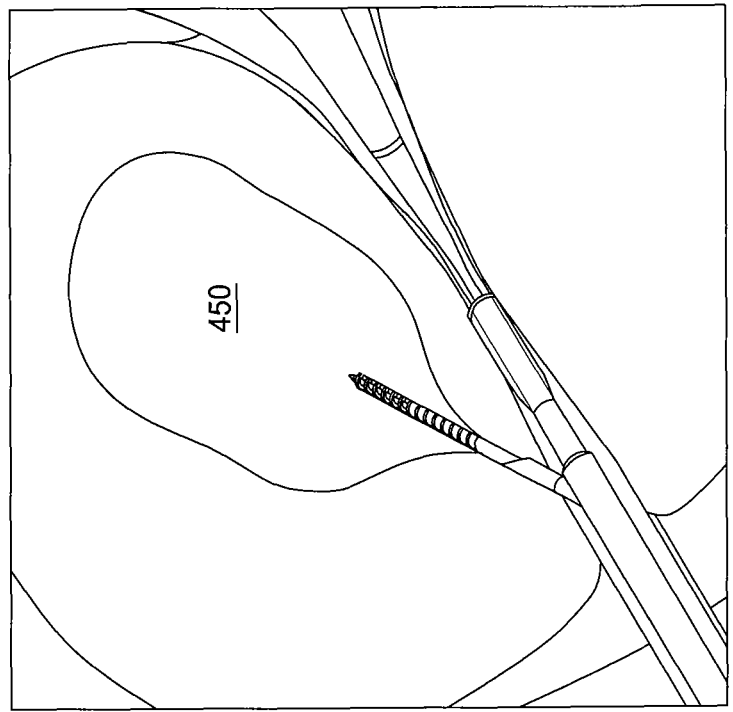
Figure 21A:
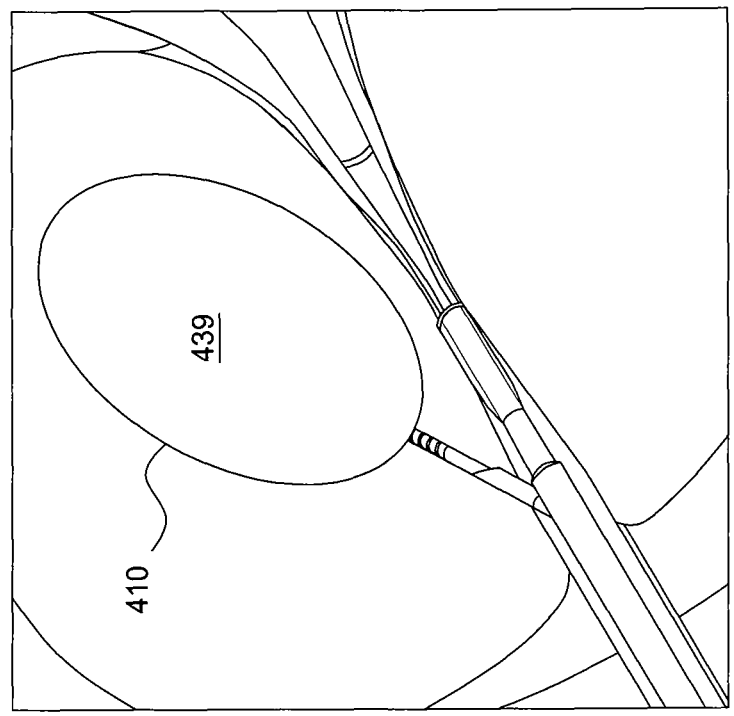

In another embodiment, a radio frequency (RF) probe 430 with a built-in aspiration device may be used to remove the prostatic tissue around the urethra 15. FIG. 18 shows an exemplary RF probe 430 suitable for use with the various embodiments the surgical procedure described herein. The RF probe 430 is connected to a RF generator 438 and includes a longitudinal probe body 432 and a probe head 434 having an outer auger portion 437. The longitudinal body 432 is movable within an outer tube. In FIG. 19, the RF probe 430 is inserted into the prostate 10 through the cannula 120. As shown, the probe head 434 has extended out of the outer tube 435. After insertion, RF energy 439 is transmitted through the probe body 432 to the probe head 434 to treated the prostatic tissue, as shown in FIG. 20. At the same time, the RF probe 430 may be rotated 433 to activate the auger portion 437. Rotation 433 of the auger portion 437 draws the treated tissue into the outer tube 435, thereby creating the tissue cavity. FIG. 21A shows the zone 410 of tissue that may be affected by the RF energy 439. FIG. 21B shows the cavity 450 that may be created.

Figure 22B:
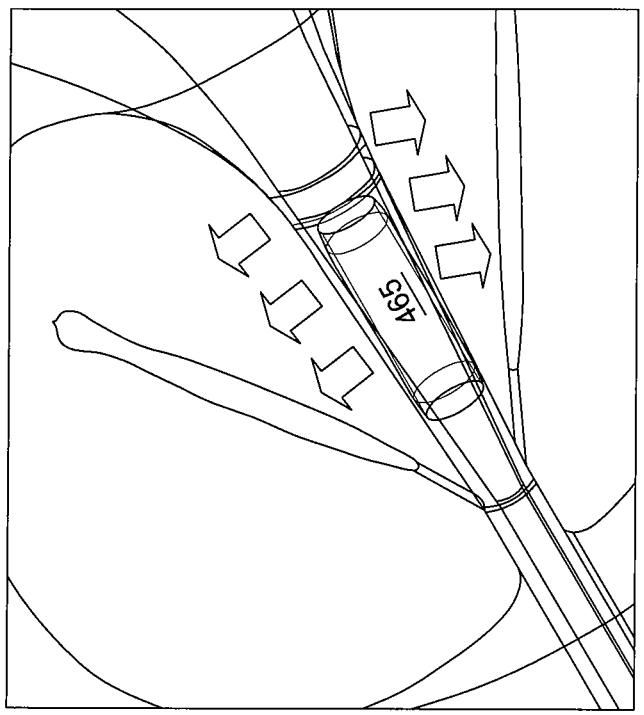
FIG. 22B illustrates implantation of a stent in the enlarged lumen.
Figure 22A:
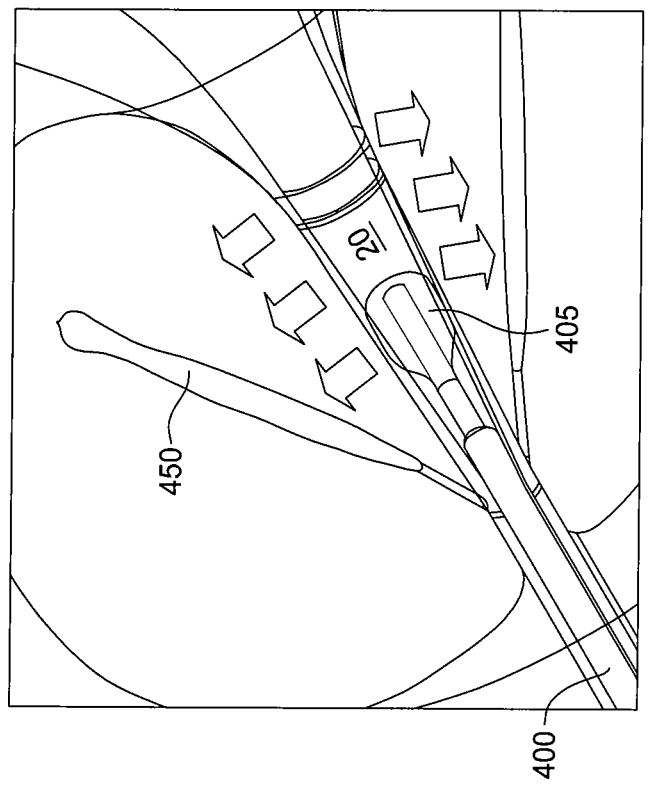
FIG. 22A illustrates expansion of the lumen using a balloon.
Figure 24B:
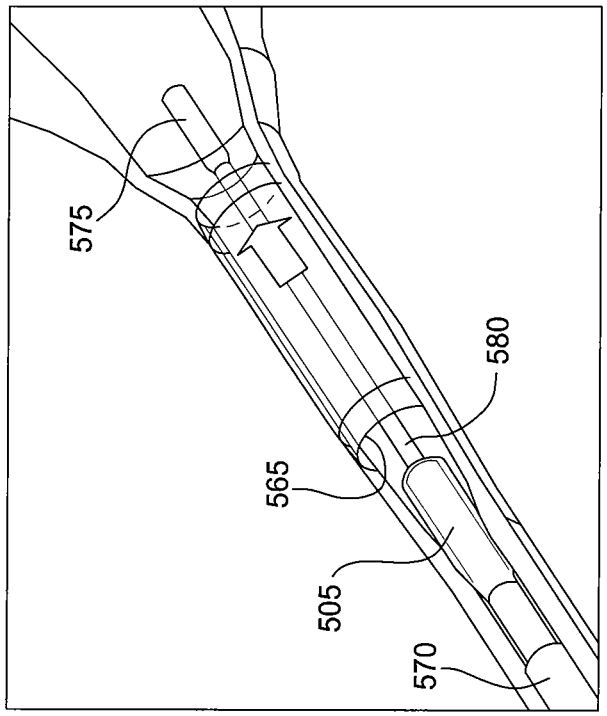
FIGS. 24A-D illustrates an embodiment of a device and process of removing a stent from the urethra.
Figure 24A:
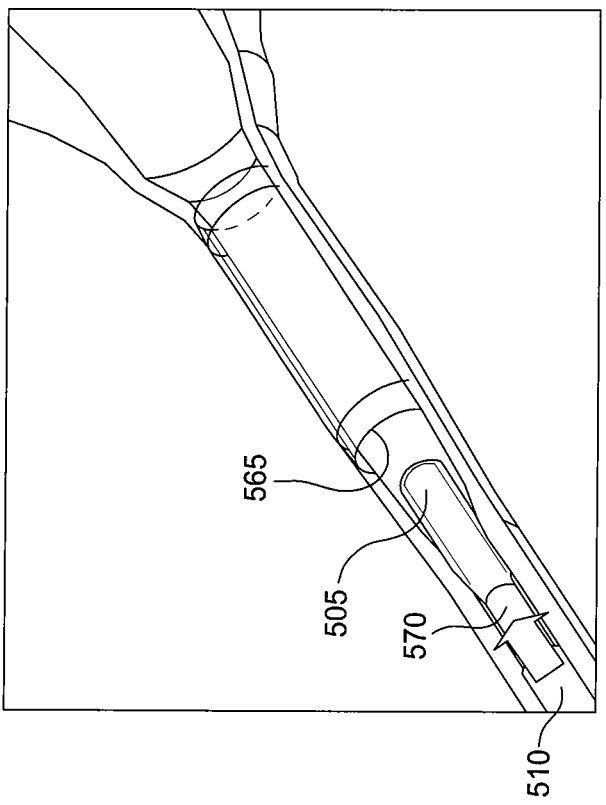
Figure 24D:
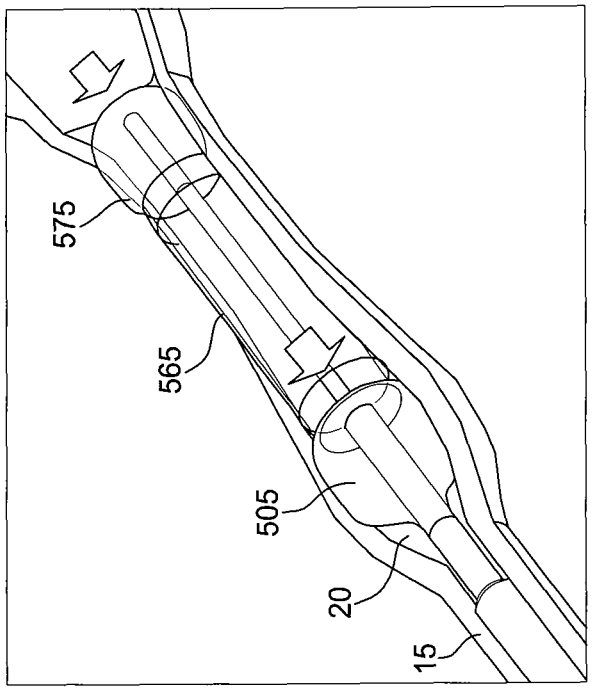
Figure 24C:
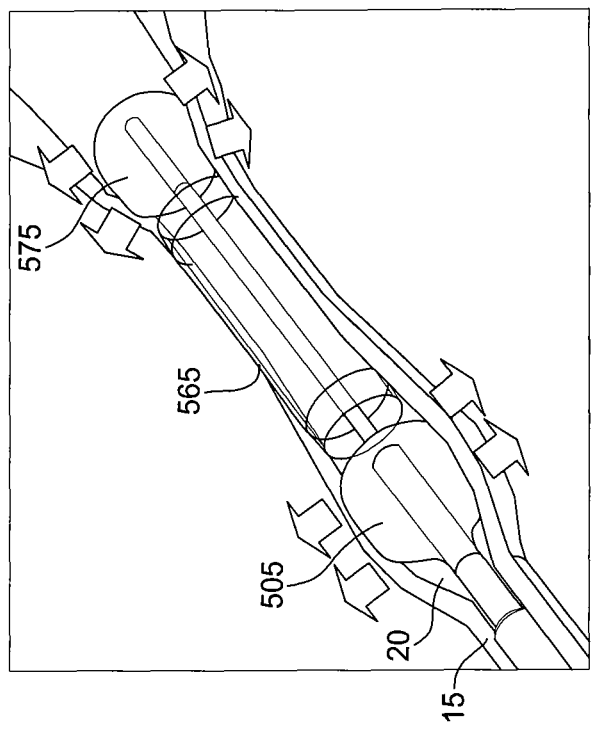

FIG. 22A shows the RF probe 430 retracted into the surgical device 400. After the cavity 450 has been created, a balloon 405 may be inflated to enlarge the lumen 20 of the urethra 15. In FIG. 22B, a urethral stent 465 may be implanted, at least temporarily, to maintain the enlarged lumen 20.

In another embodiment, the mechanical debrider and an energy probe may be used in combination. For example, after the mechanical debrider has created a cavity, a RF probe, a laser probe, or other suitable energy deliverable probe may be inserted into the prostate to apply RF, heat, or other suitable energy to treat the targeted tissue. The energy applied may assist with the control of hemostasis. In another example, the energy probe may be inserted before the mechanical probe to apply energy to the prostatic tissue. Then, the mechanical debrider may be inserted to remove the heat treated tissue. In yet another embodiment, energy may be applied before and after deployment of the mechanical debrider. Additionally, energy may also be applied during operation of the debrider. In yet another embodiment, the mechanical debrider may be attached to a RF energy source such that RF energy may be applied through the debrider. In yet another embodiment, the debrider may be fitted with a laser probe such that heat energy may be delivered from the debrider.

FIGS. 23-24 illustrate a method and device for removing a temporary stent 565. FIG. 23 illustrates a stent positioned in the enlarged lumen 20 of the urethra 15. In FIG. 24A, a stent removal device 570 is inserted into the urethra 15 and the front end is positioned just before the stent 570. The stent removal device 570 includes a catheter 510 having an expandable member such as a balloon 505 positioned at its front end. The device 570 further includes a second balloon 575 that is delivered by a conveying member 580 such as a cannula, as shown in FIG. 24B. After the first balloon 505 is properly positioned, the second balloon 575 is transported through the stent 565 and positioned behind the stent 565. Thereafter, both balloons 505, 575 are inflated to enlarge the lumen 20 of the urethra 15, as shown in FIG. 24C. In FIG. 24D, the second balloon 575 is pulled toward the first balloon 505, which also pulls the stent 565 toward the first balloon 505. After the stent 565 makes contact with the first balloon 505, the two balloons 505, 575 and the stent 565 may be retrieved and removed together from the urethra 15.

Several advantages of the embodiments of the present invention may be readily apparent to one of ordinary skill in the art. One advantage of the devices and treatment methods disclosed herein is conservation of the inner lining of the urethra, which minimizes bleeding, improves the recovery process, reduces post-operative pain, and eliminates the potential for post-surgical scar which may lead constriction of the urethra. Another advantage of the disclosed embodiments is increased tissue reduction. Yet another advantage is the treatment methods would be suitable for outpatient treatment, wherein the patient may return home after the procedure is completed. As a result of less tissue destruction, a temporary stent may be implanted to maintain the lumen and allow the patient to control urination after the surgical procedure. The potential for less post-operative complication also increases likelihood for use as an outpatient procedure.

In one embodiment, a method of removing a tissue of a prostate proximate a urethra having an inner lining includes positioning a catheter in the urethra; inserting a mechanical debrider through the catheter; positioning the mechanical debrider in the prostate proximate the tissue to be removed; rotating the mechanical debrider against the tissue; and removing the prostatic tissue, thereby forming a cavity adjacent the inner lining of the urethra.

In another embodiment, the method of removing tissue includes applying thermal energy to the tissue. In yet another embodiment, the thermal energy is applied before rotation of the debrider. In yet another embodiment, the thermal energy is applied after rotation of the debrider. In yet another embodiment, the thermal energy is applied during rotation of the debrider. In yet another embodiment, the method includes positioning an energy probe in the tissue to apply the thermal energy. In yet another embodiment, the thermal energy comprises one of RF energy, laser, and combinations thereof. In yet another embodiment, the thermal energy is applied through the debrider.

In yet another embodiment, the method includes expanding an expandable member in the urethra. In yet another embodiment, the expandable member is expanded during rotation of the mechanical debrider. In yet another embodiment, the expandable member is expanded after removing the prostatic tissue. In yet another embodiment, the expandable member is also expanded during rotation of the mechanical debrider. In yet another embodiment, the expandable member comprises an inflatable balloon.

In another embodiment, a medical device includes a catheter; an endoscope positioned in the catheter, and a mechanical debrider extending out of the catheter, wherein the debrider includes an outer tube and a tissue removal member.

In one or more of the embodiments described herein, the catheter includes an inflatable balloon.

In one or more of the embodiments described herein, the debrider further includes a spiral groove disposed on a outer portion.

In one or more of the embodiments described herein, rotation of the spiral groove draws a loosened tissue into the outer tube.

In one or more of the embodiments described herein, the removal member includes one or more blades for cutting a tissue.

In one or more of the embodiments described herein, the one or more blades comprise a flexible metal.

In one or more of the embodiments described herein, the one or more blades are adapted to flex radially outward.

In one or more of the embodiments described herein, a medical device includes an expandable member. In yet another embodiment, the expandable member comprises an inflatable balloon. In yet another embodiment, the medical device includes a third channel for supplying a fluid to the expandable member.

In one or more of the embodiments described herein, a medical device includes a tissue removal member having an adjustable diameter. In another embodiment, the debrider further includes a conveying member having a central passage. In another embodiment, the tissue removal member is movable in the central passage. In another embodiment, a length of the tissue removal member extending out of the central passage is controllable to adjust the diameter of the tissue removal member. In another embodiment, the medical device includes a cable attached to an end of the removal member. In another embodiment, the cable is retractable within the central passage to adjust a diameter of the tissue removal member. In another embodiment, the conveying member includes an auger portion.

While the foregoing is directed to embodiments of the present invention, other and further embodiments of the invention may be devised without departing from the basic scope thereof, and the scope thereof is determined by the claims that follow.

I claim:

1. A method of removing a tissue of a prostate proximate a urethra having an inner lining, comprising:
   positioning a catheter in the urethra; inserting a mechanical debrider through the catheter;
   positioning the mechanical debrider in the prostate proximate the tissue to be removed;
   rotating the mechanical debrider against the tissue;
   removing the prostatic tissue, thereby forming a first cavity adjacent the inner lining of the urethra; and
   re-positioning the mechanical debrider and forming a second cavity adjacent the urethra, wherein the first cavity and the second cavity are in direct fluid communication such that fluid can flow from the first cavity to the second cavity without entering the urethra.

2. The method of claim 1, further comprising expanding an expandable member in the urethra.

3. The method of claim 2, wherein the expandable member is expanded during rotation of the mechanical debrider.

4. The method of claim 2, wherein the expandable member comprises an inflatable balloon.

5. The method of claim 1, further comprising inserting a guide member through the catheter and into the prostate.

6. The method of claim 5, wherein the mechanical debrider is inserted through the guide member.

7. The method of claim 5, further comprising expanding an expandable member in the urethra during rotation of the debrider.

8. The method of claim 1, wherein removing the tissue is achieved via rotation of the debrider.

9. The method of claim 8, wherein the debrider comprises an auger portion for removing the tissue.

10. The method of claim 1, further comprising applying thermal energy to the tissue.

11. The method of claim 1, further comprising adjusting a diameter of the debrider.

12. The method of claim 1, further comprising enlarging a lumen of the urethra.

13. The method of claim 12, further comprising positioning a stent in the enlarged lumen.

14. The method of claim 13, further comprising enlarging the stent.

15. The method of claim 14, wherein an expandable member is used to enlarge the lumen.

16. The method of claim 13, further comprising removing the stent.

17. The method of claim 16, wherein removing the stent comprises inflating a first expandable member before the stent and a second expandable member after the stent.

18. The method of claim 1, further comprising advancing the mechanical debrider through a sidewall of the catheter.

19. The method of claim 18, wherein the mechanical debrider is advanced through the sidewall of the catheter at an angle to the catheter.

20. The method of claim 19, further comprising adjusting the angle at which the mechanical debrider is advanced through the sidewall of the catheter.

21. The method of claim 18, wherein the mechanical debrider is advanced through the sidewall of the catheter substantially parallel to the catheter.

22. The method of claim 1, further comprising:
   repeatedly re-positioning the mechanical debrider to form an additional cavity adjacent the urethra, wherein the additional cavity, the first cavity and the second cavity are in direct fluid communication thereby forming a tubular cavity and the re-positioning of the mechanical debrider is repeated until a desired length of the tubular cavity is formed.

23. A method of removing a tissue of a prostate proximate a urethra having an inner lining, comprising:
   positioning a catheter in the urethra;
   inserting a mechanical debrider through the catheter;
   positioning the mechanical debrider in the prostate proximate the prostatic tissue to be removed;
   rotating the mechanical debrider against the prostatic tissue;
   urging the prostatic tissue into a path of the rotating mechanical debrider by expanding an expandable member in the urethra during rotation of the mechanical debrider; and
   removing the prostatic tissue, thereby forming a cavity adjacent the inner lining of the urethra.

24. The method of claim 23, further comprising applying thermal energy to the prostatic tissue after forming the cavity.

25. The method of claim 24, wherein the thermal energy is applied using a thermal energy probe.

26. The method of claim 25, wherein the thermal energy probe is attached to the mechanical debrider.

27. The method of claim 23, further comprising re-positioning the mechanical debrider and forming a second cavity adjacent the urethra, wherein the first cavity and the second cavity are in direct fluid communication.

28. A method of removing a tissue of a prostate proximate a urethra having an inner lining, comprising:
   positioning a catheter in the urethra; inserting a mechanical debrider through the catheter;
   advancing the mechanical debrider through a sidewall of the catheter at an angle to the catheter;
   positioning the mechanical debrider in the prostate proximate the tissue to be removed;
   adjusting the angle of the mechanical debrider, within the prostate, to an angle substantially parallel to the urethra;
   rotating the mechanical debrider against the tissue;
   removing the prostatic tissue, thereby forming a cavity adjacent the inner lining of the urethra; and
   re-positioning the mechanical debrider and forming a second cavity adjacent the urethra, wherein the first cavity and the second cavity are in direct fluid communication.

* * * * *